(12) United States Patent
Dimopoulos et al.

(10) Patent No.: US 11,102,982 B2
(45) Date of Patent: *Aug. 31, 2021

(54) COMPOSITIONS AND METHODS USEFUL FOR THE PREVENTION OF MALARIA AND DENGUE VIRUS TRANSMISSION

(71) Applicant: THE JOHNS HOPKINS UNIVERSITY, Baltimore, MD (US)

(72) Inventors: George Dimopoulos, Baltimore, MD (US); Sarah M. Short, Baltimore, MD (US); Jose L. Ramirez, Rockville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/223,314

(22) Filed: Dec. 18, 2018

(65) Prior Publication Data

US 2019/0350207 A1 Nov. 21, 2019

Related U.S. Application Data

(63) Continuation of application No. 15/507,332, filed as application No. PCT/US2015/047321 on Aug. 28, 2015, now Pat. No. 10,165,781.

(60) Provisional application No. 62/185,005, filed on Jun. 26, 2015, provisional application No. 62/052,524, filed on Sep. 19, 2014, provisional application No. 62/042,856, filed on Aug. 28, 2014.

(51) Int. Cl.
| | |
|---|---|
| *A01N 63/20* | (2020.01) |
| *C12R 1/01* | (2006.01) |
| *A61K 35/74* | (2015.01) |
| *C12N 1/20* | (2006.01) |
| *A61K 31/7004* | (2006.01) |

(52) U.S. Cl.
CPC .......... *A01N 63/20* (2020.01); *A61K 31/7004* (2013.01); *A61K 35/74* (2013.01); *C12N 1/20* (2013.01); *C12R 1/01* (2013.01); *A61K 2300/00* (2013.01); *Y02A 50/30* (2018.01)

(58) Field of Classification Search
None
See application file for complete search history.

(56) References Cited

U.S. PATENT DOCUMENTS

| 8,583,238 B1 | 11/2013 | Heldman et al. | |
|---|---|---|---|
| 8,691,219 B2 * | 4/2014 | Martin | A01N 63/00 424/115 |
| 8,706,241 B2 | 4/2014 | Firlik et al. | |
| 9,339,039 B1 * | 5/2016 | Martin | A01N 63/00 |
| 10,165,781 B2 * | 1/2019 | Dimopoulos | C12N 1/20 |
| 2005/0074431 A1 | 4/2005 | Martin et al. | |
| 2007/0172463 A1 | 7/2007 | Martin et al. | |
| 2010/0087698 A1 | 4/2010 | Hoffman | |
| 2012/0100236 A1 | 4/2012 | Asolkar et al. | |
| 2013/0089530 A1 | 4/2013 | Rodriguez | |
| 2013/0096363 A1 | 4/2013 | Schneider et al. | |
| 2014/0058189 A1 | 2/2014 | Stubbeman | |

FOREIGN PATENT DOCUMENTS

| WO | 2013062977 A1 | 5/2013 |
|---|---|---|
| WO | 2012-110594 A1 | 8/2013 |

OTHER PUBLICATIONS

Muller, G., et al., "Efficacy of toxic sugar baits against adult cistern-dwelling Anopheles claviger" Transactions of the Royal Society of Tropical Medicine and Hygiene (2008) 102, 480-484.
Riehle, M., et al., "Using bacteria to express and display anti-Plasmodium molecules in the mosquito midgut. (2007) Int J Parasitol 37: 595-603".
Trager, W., et al., "Human malaria parasites in continuous culture" (1976) Science 193: 673-675.
Cirimotich Cm, et al.(2011) Native microbiota shape insect vector competence for human pathogens. Cell Host Microbe 10: 307-310.
Cirimotich Cm, et al.(2011) Low- and high-tech approaches to control Plasmodium parasite transmission by anopheles mosquitoes. J Trop Med 2011: 891342.
Cirimotich Cm, et al.(2011) Natural microbe-mediated refractoriness to Plasmodium infection in Anopheles Jambiae. Science 332: 855-858.
Gonzalez-Ceron L, et al.(2003) Bacteria in Midguts of Field-Collected Anopheles albimanus Block Plasmodium vivax Sporogonic Development. J Med Entomol40: 371-374.
Ramirez Jl, et al.(2012) Reciprocal tripartite interactions between the Aedes aegypti midgut microbiota, innate immune system and dengue virus influences vector competence. PLoS Negl Trop Dis 6: e1561.
Beier Ms, et al. 1994) Effects of Para-Aminobenzoi c Acid, Insulin, and Gentamicin on Plasmodium falciparum Development in Anopheline Mosquitoes (*Diptera: culicidae*). J Med Entomol 31: 561-565.
Dong Y, et al. (2009) Implication of the mosquito midgut microbiota in the defense against malaria parasites. PLoS Pathog 5: e1000423.
Xi, Z., et al. (2008) The Aedes aegypti Toll Pathway Controls Dengue Virus Infection_ PLoS Pathog 4: 12.
Azambuja P, et al. (2005) Gut microbiota and parasite transmission by insect vectors_ Trends Parasitol 21: 568-572.
Meister S, et al_ (2009) Anopheles gambiae PGRPLC-mediated defense against bacteria modulates infections with malaria parasites_ PLoS Pathog 5: e1000542.
Otoole G, et al. (2000) Biofilm fonmation as microbial development Annu Rev Microbial 54: 49-79_.
Flemming H-C, et al_ (2010) The biofilm matrix_ Nat Rev Microbiol 8: 623-633_.

(Continued)

*Primary Examiner* — Michael Barker
(74) *Attorney, Agent, or Firm* — Johns Hopkins Technology Ventures

(57) ABSTRACT

The present invention relates to the fields of malaria and dengue virus. More specifically, the present invention provides compositions and methods useful for the treatment and prevention of malaria and dengue virus. In particular embodiments, a composition comprises mosquito nectar feed and *Chromobacterium* sp_Panamam (Csp_P).

5 Claims, 16 Drawing Sheets

Specification includes a Sequence Listing.

(56) References Cited

OTHER PUBLICATIONS

Mulcahy H, et al. (2011) *Drosophila melanogaster* as an animal model for the study of Pseudomonas aeruginosa biofilm infections in vivo_ PLoS Pathog 7: e1002299_.

Duran N, et al_ (2001) Chromobacterium violaceum: a review of pharmacological and industiral perspectives_ Grit Rev Microbiol 27: 201-222.

Crezynski-Pasa Tb, et al_ (2004) Energetic metabolism of Chromobacterium violaceum_ Genet Mol Res 3: 162-166_.

Lopes Scp, et al. (2009) Violacein extracted from Chromobacterium violaceum inhibits Plasmodium growth in vitro and in vivo_ Antimicrob Agents Chemother 53: 2149-2152.

Michaels R, et al. (1965) Cyanide fonmation by Chromobacterium violaceum_ J Bacteriol 89: 106-112.

Blom D, et al_ (2011) Volatile-mediated killng of *Arabidopsis thaliana* by bacteria is mainly due to hydrogen cyanide_ Environ Microbial 77: 1000-1008_.

Vasconselos, et al_ (2003) The complete genome sequence of Chromobacterium violaceum eveals remarkable and exploitable bacterial adaptability_ Proc Natl Acad Sci USA 100: 11660-11665_.

Gallagher La, et al_ (2001) Pseudomonas aeruginosa PA01 kills Caenorhabditis elegans by cyanide poisoning_ J Bacteriol183: 6207-6214.

Broderick Ke, et al. (2008) Cyanide produced by human isolates of Pseudomonas aeruginosa contributes to ethality in *Drosophila melanogaster*. J Infect Dis 197: 457-464_.

Martin Paw, et al. (2007) *Chromobacterium subtsugae* sp_ nov., a betaproteobacterium toxic to Colorado potato beetle and other insect pests_ Int J Syst Evol Microbial 57: 993-999_.

Clayton Am, et al_ (2013) Caudal is a negative regulator of the Anopheles IMO pathway that controls resistance to Dlasmodium falciparum infection_ Dev Comp Immunol 39: 323-332.

Bahia Ac, et al. (2014) Exploring Anopheles gut bacteria for Plasmodium blocking activity_ Environmental Microbiology 16(9), 2980-2994.

Straif Sc, et al_ (1998) Midgut bacteria in Anopheles gambiae and An_ funestus (*Diptera: culicidae*) from Kenya and Mali. J Med Entomol 35: 222-226.

Lindh Jm, et al. (2005) 16S rRNA gene-based identification of midgut bacteria from field-caught Anopheles gambiae sensu lato and A funestus mosquitoes reveals new species related to known insect symbionts_ Appl Environ Microbial 7 1: 7217-7223.

Rani A, et al. (2009) Bacterial diversity analysis of larvae and adult midgut microftora using culture-dependent and ultureindependent methods in lab-reared and field-collected Anopheles stephensi-an Asian malarial vector. BMC Microbial 9: 96_.

Das S, et al. (2007) Protocol for Dengue Infections in Mosquitoes (*A. aegypti*) and Infection Phenotype Determination_ J. Vis. Exp. (5), e220, doi:10.3791/220.

Trager W, et al. (1976) Human malaria parasites in continuous culture_ Science 193: 673-675_.

Bennett Tn, et al. (2004) Novel, Rapid, and Inexpensive Cell-Based Quantification of Antimalarial Drug Effcacy. Antimicrobial Agents and Chemotherapy, May 2004, p. 1807-1810.

Lambros C, et al. (1979) Synchronization of Plasmodium falciparum erythrocytic stages in culture. J Parasitol65: pp. 18-420.

Ferrer P, et al.(2012) Antimalarial iron chelator, FBS0701, shows asexual and gametocyte Plasmodium falciparum activity and single oral dose cure in a murine malaria model. PLoS One 7: e37171.

Ramirez et al., "Chromobacterium Csp_P reduces malaria and dengue infection in vector mosquitoes and has entomopathogenic and in vitro anti-pathogen activities", PLoS Pathogens, vol. 10, Issue 10, Article No. e1004398 (Internal pp. 1-13) (Oct. 23, 2014).

* cited by examiner

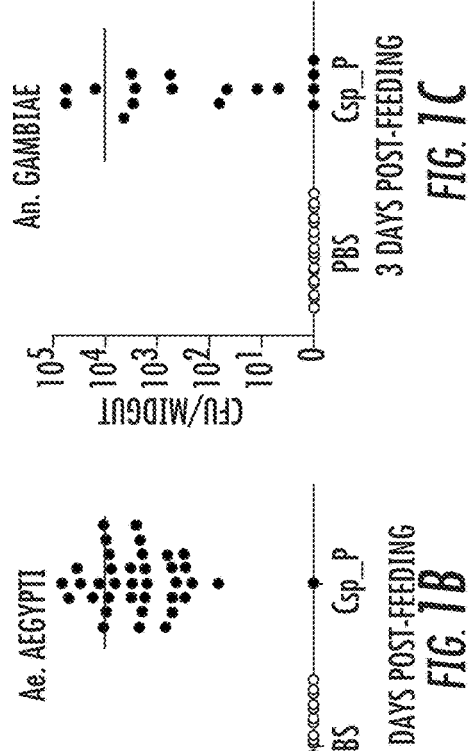
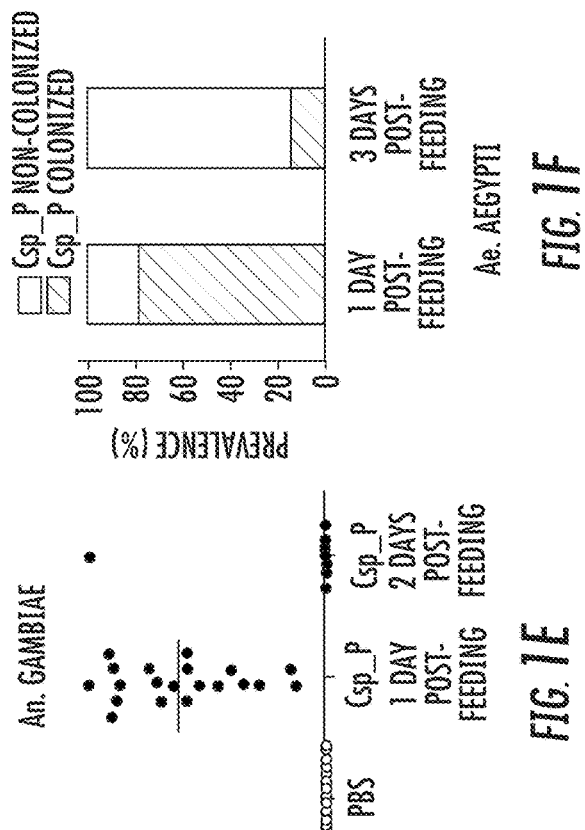
FIG. 1A, FIG. 1B, FIG. 1C, FIG. 1D, FIG. 1E, FIG. 1F

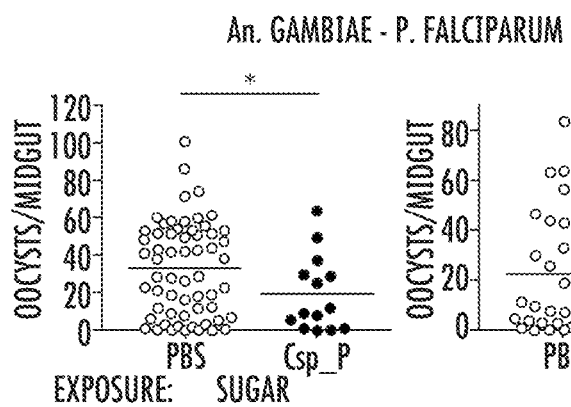
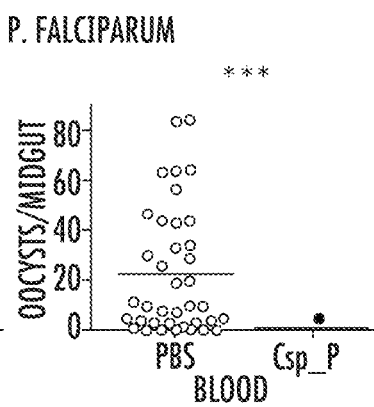
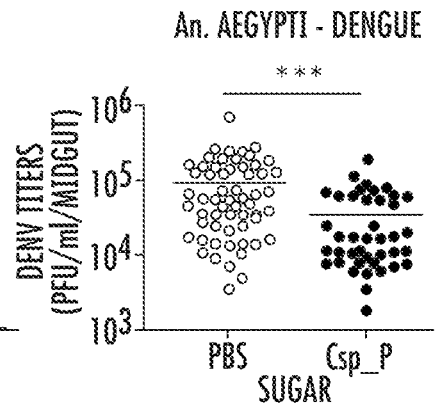
FIG. 3A  FIG. 3B  FIG. 3C
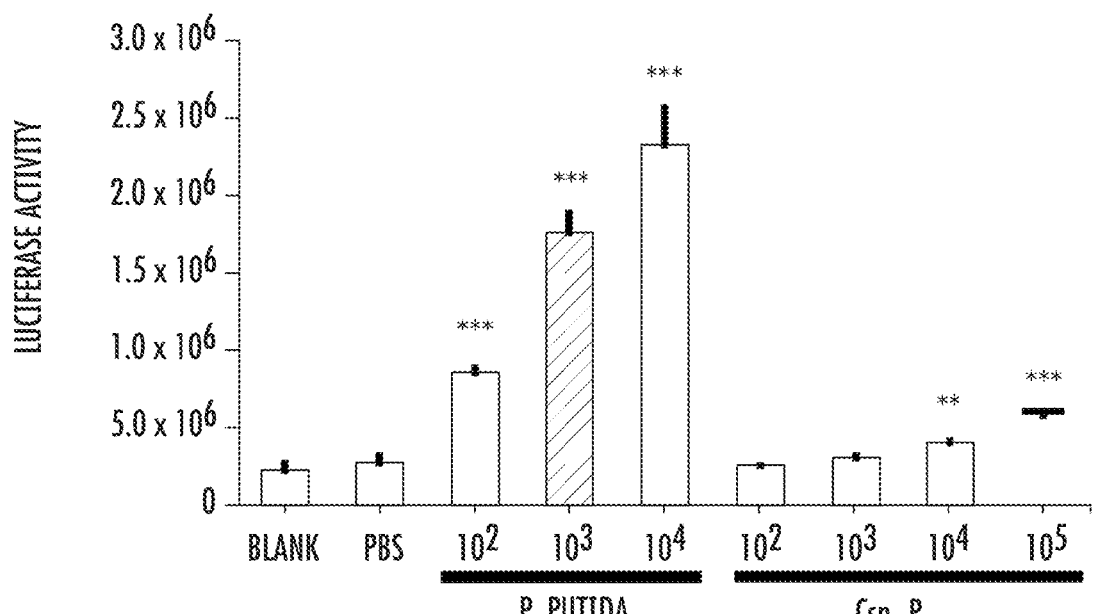
FIG. 4

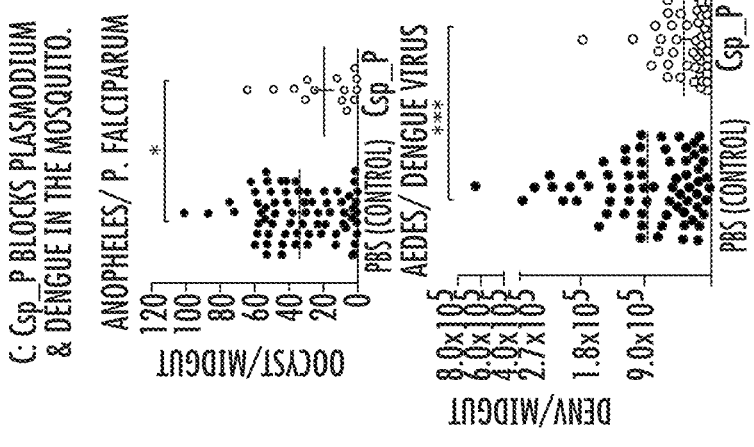
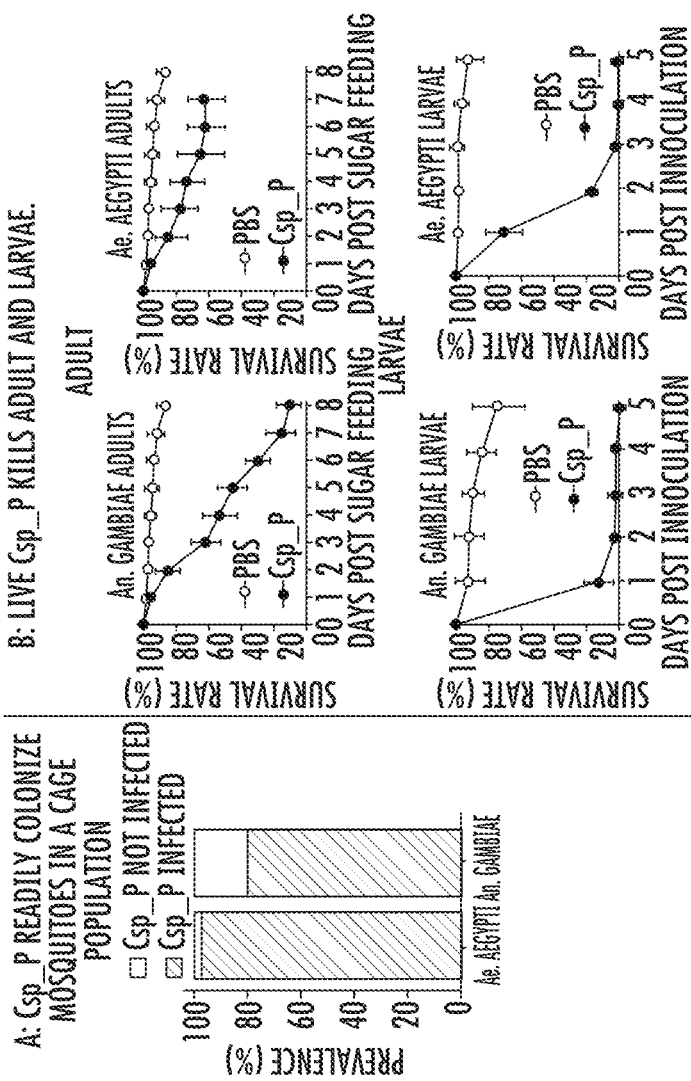
FIG. 15A
FIG. 15B
FIG. 15C

SEQUENCE LISTING

<160> NUMBER OF SEQ ID NOS: 27

<210> SEQ ID NO 1
<211> LENGTH: 1476
<212> TYPE: DNA
<213> ORGANISM: Unknown
<220> FEATURE:
<223> OTHER INFORMATION: Chromobacterium spp. (Csp_P), new species

<400> SEQUENCE: 1

```
gggaaagggg gcctgcttta ccatgcaagt cgaacggtaa cagggtgctt gcaccgctga      60
cgagtggcga acgggtgagt aatgcatcgg aatgtaccgt gtaatggggg atagctcggc     120
gaaagccgga ttaataccgc atacgccctg aggggggaaag tggggaccg aaaggcctca     180
cgttatacga gcagccgatg tctgattagc tagttggtga ggtaaaggct caccaaggcg     240
tcgatcagta gcgggtctga gaggatgatc cgccacactg ggactgagac acggcccaga     300
ctcctacggg aggcagcagt ggggaatttt ggacaatggg cgcaagcctg atccagccat     360
gccgcgtgtc tgaagaaggc cttcgggttg taaaggactt ttgtccggga gcaaatccta     420
gtggttaata accgctgggt ctgagagtac cggaagaata agcaccggct aactacgtgc     480
cagcagccgc ggtaatacgt agggtgcaag cgttaatcgg aattactggg cgtaaagcgt     540
gcgcaggcgg ttgtgcaagt ctgatgtgaa agccccgggc ttaacctggg aacggcattg     600
gagactgcac gactagagtg cgtcagaggg gggtagaatt ccgcgtgtag cagtgaaatg     660
cgtagagatg cggaggaata ccgatggcga aggcagcccc ctgggatgac actgacgctc     720
atgcacgaaa gcgtggggag caaacaggat tagataccct ggtagtccac gccctaaacg     780
atgtcaacta gctgttgggg gtttgaatcc ttggtagcgt agctaacgcg agaagttgac     840
cgcctgggga gtacggccgc aaggttaaaa ctcaaaggaa ttgacgggga cccgcacaag     900
cggtggatga tgtggattaa ttcgatgcaa cgcgaaaaac cttacctggt cttgacatgt     960
aacgaacgct gcagagatgt ggtggtgccc gaaagggagc gttaacacag gtgctgcatg    1020
gctgtcgtca gctcgtgtcg tgagatgttg ggttaagtcc cgcaacgagc gcaacccttg    1080
ccattagttg ccatcattaa gttgggcact ctaatgggac tgccggtgac aaaccggagg    1140
aaggtgggga tgacgtcaag tcctcatggc ccttatgacc agggcttcac acgtcataca    1200
atggtcggta cagagggtcg cgaagccgcg aggtggagcc aatctcataa aaccgatcgt    1260
agtccggatc gcactctgca actcgagtgc gtgaagtcgg aatcgctagt aatcgcagat    1320
cagcatgctg cggtgaatac gttcccgggt cttgtacaca ccgcccgtca ccatgggag    1380
gtgagtttca ccagaagtgg gtaggctaac cgtaaggagg ccgcttacca cggtgggatt    1440
catgactggg gggaagtcgt aacaagggca agcccc                              1476
```

<210> SEQ ID NO 2
<211> LENGTH: 20
<212> TYPE: DNA
<213> ORGANISM: Artificial Sequence
<220> FEATURE:
<223> OTHER INFORMATION: Csp_P hydrogen cyanide synthase B forward primer

<400> SEQUENCE: 2

```
agggcgtaac cctggactat                                                  20
```

```
<210> SEQ ID NO 3
<211> LENGTH: 20
<212> TYPE: DNA
<213> ORGANISM: Artificial Sequence
<220> FEATURE:
<223> OTHER INFORMATION: Csp_P hydrogen cyanide synthase B reverse
      primer

<400> SEQUENCE: 3
ccgaaggaac tggcttcgta                                          20

<210> SEQ ID NO 4
<211> LENGTH: 22
<212> TYPE: DNA
<213> ORGANISM: Artificial Sequence
<220> FEATURE:
<223> OTHER INFORMATION: Aedes aegypti Ribosomal S7 forward primer

<400> SEQUENCE: 4
gggacaaatc ggccaggcta tc                                       22

<210> SEQ ID NO 5
<211> LENGTH: 22
<212> TYPE: DNA
<213> ORGANISM: Artificial Sequence
<220> FEATURE:
<223> OTHER INFORMATION: Aedes aegypti ribosomal S7 reverse primer

<400> SEQUENCE: 5
tcgtggacgc ttctgcttgt tg                                       22

<210> SEQ ID NO 6
<211> LENGTH: 21
<212> TYPE: DNA
<213> ORGANISM: Artificial Sequence
<220> FEATURE:
<223> OTHER INFORMATION: Aedes aegypti defensin-C forward primer

<400> SEQUENCE: 6
ttgtttgctt cgttgctctt t                                        21

<210> SEQ ID NO 7
<211> LENGTH: 21
<212> TYPE: DNA
<213> ORGANISM: Artificial Sequence
<220> FEATURE:
<223> OTHER INFORMATION: Aedes aegypti defensin-C reverse primer

<400> SEQUENCE: 7
atctcctaca ccgaacccac t                                        21

<210> SEQ ID NO 8
<211> LENGTH: 20
<212> TYPE: DNA
<213> ORGANISM: Artificial Sequence
<220> FEATURE:
<223> OTHER INFORMATION: Aedes aegypti cecropin-G forward primer

<400> SEQUENCE: 8
ccaagccttg tgaaccagta                                          20

<210> SEQ ID NO 9
<211> LENGTH: 18
<212> TYPE: DNA
<213> ORGANISM: Artificial Sequence
<220> FEATURE:
<223> OTHER INFORMATION: Aedes aegypti cecropin-G reverse primer
```

-continued

```
<400> SEQUENCE: 9
ggccacctgc ttcagact                                                    18

<210> SEQ ID NO 10
<211> LENGTH: 19
<212> TYPE: DNA
<213> ORGANISM: Artificial Sequence
<220> FEATURE:
<223> OTHER INFORMATION: Aedes aegypti cecropin-E forward primer

<400> SEQUENCE: 10
cgaagccggt ggtctgaag                                                   19

<210> SEQ ID NO 11
<211> LENGTH: 21
<212> TYPE: DNA
<213> ORGANISM: Artificial Sequence
<220> FEATURE:
<223> OTHER INFORMATION: Aedes aegypti cecropin-E reverse primer

<400> SEQUENCE: 11
actacgggaa gtgctttctc a                                                21

<210> SEQ ID NO 12
<211> LENGTH: 21
<212> TYPE: DNA
<213> ORGANISM: Artificial Sequence
<220> FEATURE:
<223> OTHER INFORMATION: Aedes aegypti lysozyme C forward primer

<400> SEQUENCE: 12
ccacggcaac tggatatgtc t                                                21

<210> SEQ ID NO 13
<211> LENGTH: 21
<212> TYPE: DNA
<213> ORGANISM: Artificial Sequence
<220> FEATURE:
<223> OTHER INFORMATION: Aedes aegypti lysozyme C reverse primer

<400> SEQUENCE: 13
tctgcgtcac cttggtggta t                                                21

<210> SEQ ID NO 14
<211> LENGTH: 23
<212> TYPE: DNA
<213> ORGANISM: Artificial Sequence
<220> FEATURE:
<223> OTHER INFORMATION: Anopheles gambiae PGRP-LC forward primer

<400> SEQUENCE: 14
agaataccac actaaggcac agt                                              23

<210> SEQ ID NO 15
<211> LENGTH: 23
<212> TYPE: DNA
<213> ORGANISM: Artificial Sequence
<220> FEATURE:
<223> OTHER INFORMATION: Anopheles gambiae PGRP-LC reverse primer

<400> SEQUENCE: 15
agacttacga tcctggtaaa tgt                                              23
```

<210> SEQ ID NO 16
<211> LENGTH: 22
<212> TYPE: DNA
<213> ORGANISM: Artificial Sequence
<220> FEATURE:
<223> OTHER INFORMATION: Anopheles gambiae cecropin 1 forward primer

<400> SEQUENCE: 16
ccagagacca accaaccacc aa                                              22

<210> SEQ ID NO 17
<211> LENGTH: 21
<212> TYPE: DNA
<213> ORGANISM: Artificial Sequence
<220> FEATURE:
<223> OTHER INFORMATION: Anopheles gambiae cecropin 1 reverse primer

<400> SEQUENCE: 17
gcactgccag cacgacaaag a                                               21

<210> SEQ ID NO 18
<211> LENGTH: 20
<212> TYPE: DNA
<213> ORGANISM: Artificial Sequence
<220> FEATURE:
<223> OTHER INFORMATION: Anopheles gambiae FBN9 forward primer

<400> SEQUENCE: 18
ccaagatgtc gggcaagtat                                                 20

<210> SEQ ID NO 19
<211> LENGTH: 20
<212> TYPE: DNA
<213> ORGANISM: Artificial Sequence
<220> FEATURE:
<223> OTHER INFORMATION: Anopheles gambiae FBN9 reverse primer

<400> SEQUENCE: 19
ttgtggtacg tcagcgagtc                                                 20

<210> SEQ ID NO 20
<211> LENGTH: 20
<212> TYPE: DNA
<213> ORGANISM: Artificial Sequence
<220> FEATURE:
<223> OTHER INFORMATION: Anopheles gambiae TEP1 forward primer

<400> SEQUENCE: 20
atgctctgct gtcgtttgtg                                                 20

<210> SEQ ID NO 21
<211> LENGTH: 20
<212> TYPE: DNA
<213> ORGANISM: Artificial Sequence
<220> FEATURE:
<223> OTHER INFORMATION: Anopheles gambiae TEP1 reverse primer

<400> SEQUENCE: 21
ttcgtgtcct ccggtatttc                                                 20

<210> SEQ ID NO 22
<211> LENGTH: 19
<212> TYPE: DNA
<213> ORGANISM: Artificial Sequence
<220> FEATURE:
<223> OTHER INFORMATION: Anopheles gambiae LRRD7 forward primer -continued

```
<400> SEQUENCE: 22
tcggtgagca acagtttga                                              19

<210> SEQ ID NO 23
<211> LENGTH: 19
<212> TYPE: DNA
<213> ORGANISM: Artificial Sequence
<220> FEATURE:
<223> OTHER INFORMATION: Anopheles gambiae LRRD7 reverse primer

<400> SEQUENCE: 23
cttcattccc gctaatgct                                              19

<210> SEQ ID NO 24
<211> LENGTH: 20
<212> TYPE: DNA
<213> ORGANISM: Artificial Sequence
<220> FEATURE:
<223> OTHER INFORMATION: Anopheles gambiae defensin 1 forward primer

<400> SEQUENCE: 24
gcggttccaa agttccgaca                                             20

<210> SEQ ID NO 25
<211> LENGTH: 20
<212> TYPE: DNA
<213> ORGANISM: Artificial Sequence
<220> FEATURE:
<223> OTHER INFORMATION: Anopheles gambiae defensin 1 reverse primer

<400> SEQUENCE: 25
agcgggacac aaaattgttc                                             20

<210> SEQ ID NO 26
<211> LENGTH: 20
<212> TYPE: DNA
<213> ORGANISM: Artificial Sequence
<220> FEATURE:
<223> OTHER INFORMATION: Anopheles gambiae Rel2 forward primer

<400> SEQUENCE: 26
cggagaagtc gaagaaaacg                                             20

<210> SEQ ID NO 27
<211> LENGTH: 20
<212> TYPE: DNA
<213> ORGANISM: Artificial Sequence
<220> FEATURE:
<223> OTHER INFORMATION: Anopheles gambiae Rel2 reverse primer

<400> SEQUENCE: 27
cacaggcaca cctgattgag                                             20
```

COMPOSITIONS AND METHODS USEFUL FOR THE PREVENTION OF MALARIA AND DENGUE VIRUS TRANSMISSION

CROSS-REFERENCE TO RELATED APPLICATIONS

This application is a Continuation of U.S. patent application Ser. No. 15/507,332, filed Feb. 28, 2017, now U.S. Pat. No. 10,165,781, granted Jan. 1, 2019, which is a 35 U.S.C. § 371 U.S. national entry of International Application PCT/US2015/047321, having an international filing date of Aug. 28, 2015, which claims the benefit of U.S. Provisional Application No. 62/185,005, filed Jun. 26, 2015, U.S. Provisional Application No. 62/052,524, filed Sep. 19, 2014, and U.S. Provisional Application No. 62/042,856, filed Aug. 28, 2014, all of which are incorporated herein by reference in their entireties.

STATEMENT OF GOVERNMENTAL INTEREST

This invention was made with government support under grant numbers AI061576, AI059492, AI078997, AI080161, awarded by the National Institutes of Health. The government has certain rights in the invention.

FIELD OF THE INVENTION

The present invention relates to the fields of malaria and dengue virus. More specifically, the present invention provides compositions and methods useful for the prevention of malaria and dengue transmission.

INCORPORATION-BY-REFERENCE OF MATERIAL SUBMITTED ELECTRONICALLY

This application contains a sequence listing. It has been submitted electronically via EFS-Web as an ASCII text file entitled "P12694-04_ST25.txt." The sequence listing is 7,980 bytes in size, and was created on Aug. 27, 2015. It is hereby incorporated by reference in its entirety.

BACKGROUND OF THE INVENTION

*Plasmodium* and dengue virus, the causative agents of the two most-devastating vector-borne diseases, malaria and dengue, are transmitted by the two most important mosquito vectors, *Anopheles gambiae* and *Aedes aegypti*, respectively. The lack of vaccines and effective drugs, along with insecticide resistance, has rendered the control of these important pathogens cumbersome, and call for the development of novel disease transmission blocking strategies.

SUMMARY OF THE INVENTION

*Plasmodium* and dengue virus, the causative agents of the two most-devastating vector-borne diseases, malaria and dengue, are transmitted by the two most important mosquito vectors, *Anopheles gambiae* and *Aedes aegypti*, respectively. The present inventors discovered that *Chromobacterium* sp_Panamam (Csp_P) can effectively colonize the midgut of *An. gambiae* and *Ae. Aegypti* mosquitoes when introduced through an artificial nectar meal. Csp_P exposure reduces the survival of both the larval and adult mosquito stages, and thereby represents a potent entomopathogenic agent. Because Csp_P blocks *Plasmodium falciparum* and dengue virus infection in the mosquito gut, it also represents a disease transmission blocking agent. The entomopathogenic and anti-pathogen properties of Csp_P render it a strong candidate for malaria and dengue control strategies.

The entomopathogenic, in vivo anti-dengue and anti-*Plasmodium* properties of Csp_P make this bacterium a particularly strong candidate for use in novel control strategies for these two most important vector-borne diseases. In particular embodiments, Csp_P can be used in a disease control strategy based on the direct exposure of larval or adult stage mosquitoes to this bacterium, or the entomopathogenic and anti-pathogen agents (molecules) it produces. Exposure of larvae to Csp_P or its produced entomopathogenic extracts or purified molecules could be achieved through direction administration in the breeding water. Exposure of adult mosquitoes to Csp_P or its produced antipathogen extracts or purified molecules could be achieved through artificial nectar feeding.

Csp_P is the first identified bacterium that exerts broad-spectrum anti-pathogen activity against *Plasmodium* and dengue virus in their respective vectors, along with entomopathogenic activity against larval and adult stages of *An. gambiae* and *Ae. Aegypti*. Csp_P is the first bacterium that has been shown to mediate these diverse activities through secreted molecules.

Accordingly, in one aspect, the present invention provides compositions useful for the prevention of malaria and dengue virus transmission. In certain embodiments, the compositions are useful as a general mosquitocidal agent and/or a malaria and dengue transmission-blocking agent. In particular embodiments, a composition comprises mosquito nectar feed and *Chromobacterium* sp_Panamam (Csp_P). In a specific embodiment, Csp-P is comprises a biofilm. The biofilm can be fresh or desiccated. In another embodiment, Csp-P is comprises a culture. In a further embodiment, Csp_P comprises a supernatant. In yet another embodiment, Csp_P comprises a filtrate. In certain embodiments, Csp_P has the 16s rDNA gene sequence of SEQ ID NO: 1. In certain embodiments, the nectar feed comprises one or more of sucrose, dextrose and fructose.

The present invention also provides methods for controlling malaria and dengue virus transmission via mosquitoes comprising the step of applying a composition described herein in an area where the mosquitoes are to be controlled. In specific embodiments, the mosquitoes comprise *Anopheles* and/or *Aedes* mosquitoes. In more specific embodiments, the *Anopheles* mosquitoes comprise *Anopheles gambiae* mosquitoes. In other embodiments, the *Aedes* mosquitoes comprise *Aedes aegypti* mosquitoes.

In another specific embodiment, the present invention provides compositions comprising a biofilm, supernatant, filtrate or extract of a biologically pure culture of *Chromobacerium* sp. (Csp_P). In one embodiment, the biologically pure culture of Csp_P has the 16S rDNA gene sequence of SEQ ID NO:1.

In further embodiments, the present invention provides a method for controlling *Anopheles* and *Aedes* mosquitoes comprising applying in an area where the mosquitoes are to be controlled a composition comprising an effective insect control amount of a supernatant, filtrate or extract of a biologically pure culture of Csp_P. In a specific embodiment, the composition further comprises a sugar source. In more particular embodiments, the sugar comprises sucrose, dextrose and/or fructose. In certain embodiments, the Csp_P is the bacteria having the characteristics of ATCC Designation No. PTA-121570.

BRIEF DESCRIPTION OF THE FIGURES

FIG. 1A-1F. Csp_P colonization of the mosquito midgut. All mosquitoes were exposed to Csp_P via sugar meal. To introduce Csp_P via sugar meal, adults were allowed to feed for 24 h on 1.5% sucrose containing Csp_P liquid culture at a final concentration of ~$10^8$ CFU/ml for *An. gambiae* and ~$10^6$ (A, B) or $10^{10}$ (F) CFU/ml for *Ae. aegypti*. For antibiotic treated mosquitoes, the prevalence of Csp_P was measured in *Ae. aegypti* and *An. gambiae* midguts at 3 days post-exposure (FIG. 1A). The number of colony forming units (CFUs) of Csp_P was also measured in the midguts of (FIG. 1B) *Ae. aegypti* and (FIG. 1C) *An. gambiae* 3 days after exposure to Csp_P. Experiments for antibiotic treated *Ae. aegypti* and *An. gambiae* were replicated at least three times. Final sample sizes: n *Ae. aegypti*/PBS=37; n *Ae. aegypti*/Csp_P=37; n *An. gambiae*/PBS=30; n *An. gambiae*/Csp_P=17. For septic (i.e., non-antibiotic treated) mosquitoes, the prevalence and bacterial load of Csp_P was measured in *An. gambiae* midguts at 1 and 2 days post exposure (FIG. 1D, FIG. 1E). Experiments for septic *An. gambiae* were replicated twice. Final sample sizes: nAn. *gambiae*/PBS=30; n *An. gambiae*/Csp_P/Day 1=20; n *An. gambiae*/Csp_P/Day 2=8. Prevalence of Csp_P was measured in *Ae. aegypti* midguts at 1 and 3 days post exposure (FIG. 1F). Experiments for septic *Ae. aegypti* were replicated twice. Final sample sizes: n *Ae. aegypti*/Csp_P/Day 1=19; n *Ae. aegypti*/Csp_P/Day 3=20. Horizontal lines indicate mean values. The following transformation was applied to all raw CFU data: y=log 10 (x+1), where x=original CFU count and y=plotted data values.

(FIG. 2A) PBS=149; (FIG. 2A) Csp_P=146; FIG. 2(B) PBS=70; (FIG. 2B) Csp_P=70. Ingestion of Csp_P significantly decreased survival in sugar-fed septic (i.e., not treated with antibiotics) *An. gambiae* (FIG. 2C, p<0.0001). In septic *Ae. aegypti*, survival was significantly decreased after feeding on a $10^{10}$ CFU/ml sugar meal (FIG. 2D, p<0.0001) but not after feeding on a $10^6$ CFU/ml sugar meal (FIG. 2D, p=0.08). Experiments in FIG. 2C and FIG. 2D were replicated twice. Total sample sizes: (FIG. 2C) PBS=95; (FIG. 2C) Csp_P=124; (FIG. 2D) PBS=185; (FIG. 2D) Csp10^6=223; (FIG. 2D) Csp10 =226. To introduce Csp_P via blood meal, Csp_P liquid culture (~$10^8$ CFU/ml) was mixed 1:1 with human blood/serum and fed to septic *An. gambiae* (FIG. 2E) and *Ae. aegypti* (FIG. 2F) adults. Experiments were replicated three times with total sample sizes: (FIG. 2E) PBS=59; (FIG. 2E) Csp_P=51; (FIG. 2F) PBS=37; (FIG. 2F) Csp_P=62. The effects of †Csp_P on larval mortality were also tested by placing 2- to 4-day-old *An. gambiae* (FIG. 2G) and *Ae. aegypti* (FIG. 2H) larvae in water containing Csp_P at a starting concentration of $10^6$ CFU/ml and monitoring survival over 5 days. Experiments were replicated 2-3 times with final sample sizes: (FIG. 2G) PBS=80; (FIG. 2G) Csp_P=60; (FIG. 2H) PBS=100; (FIG. 2H) Csp_P=60. P values reported above were obtained by performing pairwise Log-Rank Tests between PBS and Csp_P treatments. Survival curves were fitted using the Kaplan-Meier method. Vertical tick-marks indicate censored samples; in FIG. 2C and FIG. 2D multiple individuals were dissected on each day to measure Csp_P prevalence and bacterial load for FIG. 1.

FIG. 3A-3C. Csp_P reduces mosquitoes' susceptibility to malaria and dengue infection. In (FIG. 3A) and (FIG. 3C), antibiotic-treated adults were allowed to feed for 24 h on 1.5% sucrose containing Csp_P liquid culture at a final concentration of ~$10^8$ CFU/ml for *An. gambiae* (FIG. 3A) and ~$10^6$ CFU/ml for *Ae. aegypti* (FIG. 3C). After introduction of Csp_P via the sugar meal, *An. gambiae* mosquitoes were given a blood meal that contained *P. falciparum*, and *Ae. aegypti* mosquitoes were given a blood meal that contained dengue virus. In (FIG. 3B), Csp_P ($10^6$ CFU/ml) was introduced concurrently with *P. falciparum* via blood meal through blood feeding of antibiotic treated *An. gambiae*. In all experiments, PBS was used as the non-Csp_P-exposed control. At 7 days after infection, midguts were dissected. Oocysts were counted in *P. falciparum*-infected *An. gambiae* females, and dengue virus titers were assayed in dengue-infected *Ae. aegypti* females by conducting standard plaque assays. Experiments were initiated using similar numbers of adult females in each treatment (FIG. 3A, FIG. 3B starting numbers=45-50/trtmt, C starting numbers=30-40/treatment). All experiments were replicated at least three times with final samples sizes: (FIG. 3A) PBS=67, (FIG. 3A) Csp_P=14, (FIG. 3B) PBS=43, (FIG. 3B) Csp_P=8, (FIG. 3C) PBS=68, (FIG. 3C) Csp_P=45. Differences between treatments were assessed by Mann-Whitney test (*, p<0.05; ***, p<0.001).

FIG. 4. Csp_P elicits immune gene expression in the mosquito. Induction of the Cec1 promoter in the SUA-5B cell-line exposed to *P. putida* and *Chromobacterium* sp_Panamam Csp_P. SUA5B cells expressing a luciferase reporter gene driven by a Cec1 promoter were exposed to increasing concentrations of Csp_P and *P. putida* bacteria. Differences between bacteria treated samples and PBS control samples were assessed by Dunnett's Multiple Comparison Test (, p<0.01; *, p<0.001).

(FIG. 5A) planktonic state liquid culture, (FIG. 5B) biofilm supernatant, ([[c]]FIG. 5C) fresh biofilm, (FIG. 5D) desiccated biofilm, and (FIG. 5E) heat inactivated biofilm. (FIG. 5A) Csp_P 36-h biofilm has anti-parasite activity against asexual-stage *P. falciparum*. Csp_P cultures were filtered using a 0.2-µm filter and mixed with ring-stage *P. falciparum* parasite cultures. SYBR green I was then added to each sample, and inhibition of asexual-stage *P. falciparum* by Csp_P was measured by assaying fluorescence relative to the negative control (parasite medium, standardized to 0% inhibition). Chloroquine was used as a positive control and standardized to 100% inhibition. We performed a Tukey's test on the raw data to determine whether each bacterial treatment differed significantly from the PBS+LB control (***p<0.001). (FIG. 5B) Csp_P has anti-parasite activity against ookinete-stage *P. falciparum*. Csp_P bacterial preparations were filtered using a 0.2-µm filter and mixed with blood taken from female Swiss Webster mice infected with *Renilla* luciferase-expressing transgenic *P. berghei*. Ookinete-stage *P. berghei* parasite counts were determined using the *Renilla* luciferase assay system, and percent inhibition by Csp_P was calculated relative to the negative control (PBS+LB control, standardized to 0% inhibition). We performed a Tukey's test to determine whether each bacterial treatment differed significantly from the control (*p<0.05, ***, p<0.001). (FIG. 5C) Csp_P 42-h biofilm has anti-parasite activity against gametocyte-stage *P. falciparum*. Csp_P cultures were filtered using a 0.2-μm filter and mixed with gametocyte-stage *P. falciparum* cultures. Erythrocytes were examined for gametocytes using Giemsa-stained blood films collected 3 days after Csp_P exposure. The red X indicates that the supernatant caused hemolysis and was therefore unusable. We determined gametocyte density per 1000 RBCs for each sample and performed a Tukey's test to determine whether each bacterial treatment significantly differed from the PBS+LB control (*p<0.05, *p<0.001). (FIG. 5D) Csp_P has antidengue activity. Each Csp_P bacterial preparation (75 μl, unfiltered) was mixed with 75 μl MEM containing dengue virus serotype 2 and incubated at room temperature for 45 min. Samples were then filtered through a 0.2-μm filter and used to infect BHK21-15 cells. Percent inhibition was calculated as the percent decrease in PFU/ml relative to the negative control (PBS+LB, standardized to 0% inhibition). We analyzed the significance of pairwise comparisons between each treatment and the control using a Tukey's test (*, p<0.001). (FIG. 5E) Csp_P has anti-dengue activity when virus is suspended in human blood. Biofilms from multiple bacteria were tested for anti-dengue activity. All bacteria tested were isolated from field-caught *Ae. aegypti* mosquitoes. The biofilm from each species was grown for 48 h at room temperature, and dengue virus mixed 1:1 with human blood was added directly to the biofilm. After a 45-min incubation, the virus+blood/bilofilm solution was filtered and used to infect C6/36 cells. Biofilm sup=biofilm supernatant, H. I. biofilm=heat inactivated biofilm, dess. biofilm=desiccated biofilm resuspended in 1×PBS.

(FIG. 9A) Anti-dengue activity of fresh Csp_P biofilm is only weakly present after 24 h of growth at room temperature and becomes highly potent after 48 h of growth. Dengue virus was mixed 1:1 with human blood and directly exposed to Csp_P biofilm grown for 24 or 48 h. Samples were incubated for 45 min and then collected, filtered, and used to infect C6/36 cells. (FIG. 9B) Dengue virus particles are not sequestered by Csp_P biofilm. We mixed dengue virus with Csp_P biofilm and incubated the mixture for 45 min. We then centrifuged samples and used qRT-PCR to quantify viral RNA in the supernatant of the experimental (biofilm+DENV) and control (LB+DENV) treatments.

(FIG. 10A) Assessing changes in pH caused by Csp_P biofilm. We exposed dengue virus to Csp_P biofilm, incubated for 45 min, and measured the pH of the medium. (FIG. 10B) Assessing the effect of pH on dengue virus infectivity. We experimentally adjusted the pH of the MEM medium using NaOH and HCl to values of 5.0, 7.7, 8.5, and 10.0. We mixed the pH-adjusted media with dengue virus-laden human blood and incubated for 45 min., then collected and filtered the virus and used it to infect C6/36 cells.

FIG. 15A-15D. Live *Chromobacterium* Csp_P is a general mosquitocidal, and malaria and dengue transmission-blocking agent. Csp_P readily colonizes the gut or a large proportion of mosquitoes in a cage population when provided through artificial nectar feeding (FIG. 15A). Exposure of larvae or adult mosquitoes to Csp_P results in a significant killing (FIG. 15B). The presence of Csp_P in adult *Anopheles* and *Aedes* gut tissue blocks *Plasmodium* and dengue virus infection, respectively (FIG. 15C). The combined larvicidal and adulticidal activities of Csp_P is more potent than that of other studied *Chromobacterium* sp strains, including *Cromobacterium* subtsugae which is the active component of the agricultural biopesticide Grandevo which is marketed by Marrone Bio Innovations (FIG. 15D).

STATEMENT OF DEPOSIT

Figure 2A:
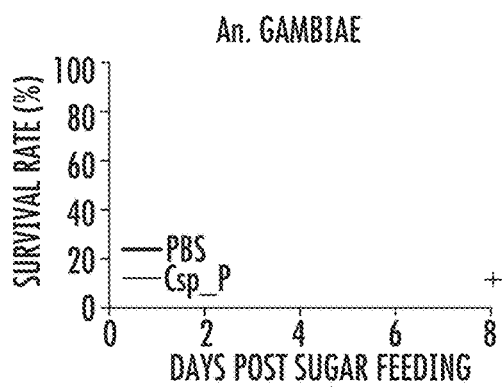
FIG. 2A-2H. Csp_P exposure causes high mortality in adults and larvae. Csp_P was experimentally introduced into the adult midgut via either a sugar meal (FIG. 2A-2D) or blood meal (FIG. 2E, FIG. 2F), and mortality was observed over 5-8 days. To introduce Csp_P via sugar meal, adults were allowed to feed for 24 h on 1.5% sucrose containing Csp_P liquid culture at a final concentration of ~$10^8$ CFU/ml for *An. gambiae* and ~$10^6$ or $10^{10}$ CFU/ml for *Ae. aegypti*. Csp_P ingestion significantly decreased survival in sugar-fed aseptic (i.e., pre-treated with antibiotics) *An. gambiae* (A, p<0.0001) and *Ae. aegypti* (B, p<0.0001). Each experiment was replicated three times. Total sample sizes.
Figure 2B:
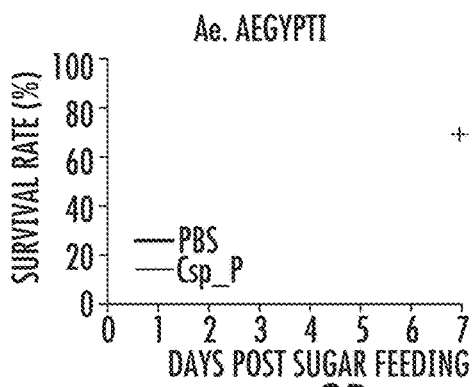

A biologically pure culture of *Chromobacterium* sp_Panamam (Csp_P) was deposited Sep. 4, 2014, under terms of the Budapest Treaty with the American Type Culture Collection (ATCC®), 10801 University Blvd., Manassas, Va. 20110, and given the accession number PTA-121570. For the purposes of this invention, any isolate having the identifying characteristics of strain Csp_P, including subcultures and variants thereof which have the identifying characteristics and activity as described herein are included.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The Gram-negative bacteria *Chromobacterium* sp_Panamam (Csp_P) was isolated from the midgut of field collected *Ae. Aegypti* mosquitoes in Panama. The genus *Chromobacterium* spp. represents soil- and water-associated bacteria of tropical and subtropical regions, and members of this genus are known to produce a variety of bioactive compounds and to form biofilms. The most extensively studied member, *Chromobacterium violaceum*, has been found to produce violacein, a violet pigment compound with potent antimicrobial, anti-parasitic, and tumoricidal activity. Csp_P can be cultured in Luria Bertani (LB) broth (at 27-37° C.) and on LB agar, on which it forms flat colonies with a tan color that becomes darker with time and are opaque when exposed to light. Csp_P does not produce violacein, but molecular characterization of its 16s rRNA gene sequence (SEQ ID NO: 1) and phylogenetic analysis showed a 98% similarity to *Chromobacterium haemolyticum* and *Chromobacterium aquaticum*, probably its two closest relatives.

Mosquito gut colonization ability: Csp_P display an exceptional ability to rapidly colonize midguts, showing a prevalence of 80% in *An. Gambiae* and 97% in *Ae. Aegypti* cage populations at 3 days after exposure. Average bacterial loads at this time point were approximately $10^5$ and $10^4$ per midgut in *Ae. Aegypti* and *An. Gambiae* females, respectively.

Entomopathogenic Activity: Supplementation of 2- to 4-day-old mosquito larvae with 50 µl of a 1.0 OD600 liquid culture of Csp_P results in almost complete mortality of *An. Gambiae* and *Ae. Aegypti* larvae over a 3- and 2-day period, respectively, when compared to the control larvae that were exposed to the normal breeding water microbiota.

Exposing antibiotic-treated *An. Gambiae* and *Ae. Aegypti* mosquitoes to a sugar source for 24 hours containing Csp_P at a final concentration of $10^8$ and $10^6$ CFU/ml, respectively, lead to a decrease in the longevity of both species when compared to non-exposed control mosquitoes. Similarly, a lower survival of septic (i.e., not pre-treated with antibiotics) *An. Gambiae* and *Ae. Aegypti* occurs after feeding on a blood meal containing Csp_P at a final concentration of $10^8$ CFU/ml.

Without being limited by any particular theory or mechanism, these studies suggest that Csp_P mediated mortality may be the result of a mosquitocidal factor or systemic infection through dissemination into the hemolymph; alternatively, its colonization of the midgut (or other tissues) might in some other way interfere with vital functions of the mosquito.

In vivo (in mosquito) anti-dengue and anti-*Plasmodium* activity: *An. Gambiae* and *Ae. Aegypti* mosquitoes colonized with Csp_P through sugar feeding prior to feeding on infectious blood displayed a significantly increased resistance to *P. falciparum* infection and dengue virus infection. The inhibition of *P. falciparum* infection was even greater when Csp_P was introduced through a blood meal at $10^6$ CFU/ml.

Csp_P exerts a direct anti-*Plasmodium* and anti-dengue effect in vitro that is independent of the mosquito: Exposure of *P. falciparum* gametocytes to 42-h fresh biofilm filtrate results in 100% inhibition ($p<0.001$) and exposure to 42-h desiccated biofilm resulted in approximately 60% inhibition ($p<0.05$, FIG. 5C) of gametocyte development. Exposure of *Plasmodium* ookinete culture to Csp_P 48-h biofilm (fresh and desiccated) and biofilm supernatant strongly blocked ookinete development.

Exposure of dengue virus to Csp_P biofilm, desiccated biofilm or biofilm supernatant abolishes dengue virus infectivity. Csp_P biofilm displays strong anti-dengue activity when the virus is suspended in human blood and is dependent on biofilm maturation, since biofilm grown for 24 hours showed weaker inhibition when compared to 48 hour biofilm. The Csp_P biofilm-associated anti-*Plasmodium* and antiviral activity is heat-sensitive, since it can be inactivated through a 24-h incubation at 90° C.

The anti-dengue activity of Csp_P biofilm is not a result of virus particle sequestration by the biofilm, or a biofilm-mediated change in the pH of the medium. Csp_P biofilm does not influence the host cells' susceptibility to dengue virus nor does it exert cytotoxic effects on host cells.

*Chromobacterium* sp_Panamam (Csp_P) is the first identified bacterium that exerts broad-spectrum anti-pathogen activity against *Plasmodium* and dengue virus in their respective vectors, along with entomopathogenic activity against larval and adult stages of *An. Gambiae* and *Ae. Aegypti*. Csp_P is the first bacterium that has been shown to mediate these diverse activities through secreted molecules. Thus, in particular embodiments, the present invention provides mosquito control products that target larval and adult stages of *Anopheles* and *Aedes* mosquitoes, though either direct exposure to the live or attenuated bacterium, or to mosquitocidal extracts from this bacterium.

I. Definitions

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, within 4-fold, within 3-fold, or within 2-fold, of a value. Where particular values are described in the application and claims, unless otherwise stated the term "about" meaning within an acceptable error range for the particular value should be assumed.

The term "substantially," as used herein, means at least about 80%, at least about 85%, at least about 90%, at least about 91%, at least about 92%, at least about 93%, at least about 94%, at least about 95%, at least about 96%, at least about 97%, at least about 98%, at least about, or at least about 99%, including, for example, at least about 99.9%. In some embodiments, the term "substantially" can mean completely, or about 100%.

As used herein, the term "administering" encompasses any method by which an insect can come into contact with a composition comprising Csp_P. An insect can be exposed to a composition by direct uptake (e.g., by feeding). Alternatively, an insect can come into direct contact with a composition comprising Csp_P. For example, an insect can come into contact with a surface or material treated with a composition comprising Csp_P. In certain embodiments, the terms can be used interchangeably with the term "treating" or "treatment."

As used herein the term "additional agent" refers to a small molecule, chemical, organic, or inorganic molecule that can be administered to or otherwise used to treat insects. In one embodiment, the "additional agent" is a pesticide. As used herein, the term "pesticide" refers to any substance or mixture of substances intended for preventing, destroying, repelling, or mitigating any pest. A pesticide can be a chemical substance or biological agent used against pests including insects that compete with humans for food, destroy property, spread disease, or are a nuisance. The term "additional agent" further encompasses other bioactive molecules such as antivirals pesticides, antifungals, antihelminthics, nutrients, sucrose and/or agents that stun or slow insect movement.

The term "whole broth culture" refers to a liquid culture containing both cells and media. If bacteria are grown on a plate, the cells can be harvested in water or other liquid, whole culture.

The term "supernatant" refers to the liquid remaining when cells grown in broth or are harvested in another liquid from an agar plate and are removed by centrifugation, filtration, sedimentation, or other means well known in the art.

The term "filtrate" refers to liquid from a whole culture that has passed through a membrane.

The term "extract" refers to liquid substance removed from cells by a solvent (water, detergent, and buffer) and separated from the cells by centrifugation, filtration or other method.

The term "metabolite" refers to a compound, substance or byproduct of a fermentation of a microorganism, or supernatant, filtrate, or extract obtained from a microorganism that has insecticidal activity.

The term "insecticidal activity" means that a substance has a detrimental effect on an insect, including but not limited to killing a target insect, increasing mortality, or inhibiting the incidence, growth, development or reproduction of a target insect.

II. *Chromobacterium* sp_Panamam (Csp_P)

The present inventors have discovered a new species of *Chromobacterium* bacterium, which exhibits insecticidal activity against *Anopheles* and *Aedes* mosquitoes. Cultures of the new bacterium are useful for control of these and other insects. The species is designated as *Chromobacterium* sp_Panamam (Csp_P).

The unique strain of the invention mediates insecticidal activity upon exposure to either larval or adult mosquito stages through the breeding water or nectar meal, respectively. Without being limited by any particular theory or mechanism, these studies suggest that Csp_P mediated mortality may be the result of a mosquitocidal factor or systemic infection through dissemination into the hemolymph; alternatively, its colonization of the midgut (or other tissues) might in some other way interfere with vital functions of the mosquito.

The full length Csp_P 16S rDNA gene sequence has been obtained and is shown in SEQ ID NO: 1. The invention is also directed to *Chromobacterium* strains which have a 16S rDNA gene sequence of SEQ ID NO: 1. Such strains may be isolated for example using appropriate nucleotide primers and identified using the full length 16S rDNA gene sequence (SEQ ID NO:1).

The present invention is further directed to methods of controlling insects using the unique bacterium of the invention. This aspect includes application of an effective insect control amount of the strain cells, supernatant, filtrate or extract containing an insecticidally active metabolite produced by the strain or combinations thereof. Csp_P has been shown to reduce the survival of both the larval and adult *Anopheles* and *Aedes* mosquito stages.

A further aspect of the invention pertains to compositions which incorporate the strain of the invention and/or compositions comprising an insecticidally active metabolite produced by the strain of the invention. Such compositions include, for example, whole cultures or suspensions of the strain; supernatants, filtrates or extracts obtained from the strain or combinations of the foregoing. Such insecticidally-active compositions may optionally include other ingredients such as an insect feeding stimulant, insect pheromone, insect attractant, fungicide, insecticide, photoactive dye, fluorescent brighteners, spreading agent, sticking agent, thickener, emulsifier, stabilizer, preservative, buffer, water, diluent or other additive as known in the art of formulation of insecticidal compositions.

The present invention is also directed to extracts obtained from the strain which have insecticidal activity. Extraction from the cells is accomplished using procedures known in the art. Exemplary procedures include, but are not limited to, adding 0.1% detergent or 0.1% CHAPS buffer to a cell pellet in equal volume of the original culture; extraction is for 30 minutes with shaking at room temperature. Cells are removed by centrifugation; the supernatant contains the toxin. The entire extract without removal of the cells is also toxic. Triton X-100 can be used as the detergent in order to carry out tests for toxicity; however, other detergents can be used to extract the toxin. In a particular embodiment, a volume of detergent or buffer to a cell pellet equal in volume to the original culture can be used for comparison of toxicity; however, one could extract in a smaller volume and may concentrate the activity.

The present invention is further directed to methods of controlling insects using the unique bacterium of the invention. This aspect includes application of an effective insect control amount of the strain, application of an effective insect control amount of a supernatant, filtrate or extract containing an insecticidally active metabolite produced by the strain or application of combinations of the foregoing. The strain, supernatant, filtrate or extract is applied, alone or in combination, in an effective insect control or insecticidal amount. For the purposes of this invention, an effective amount is defined as that quantity of microorganism cells, supernatant, filtrate or extract, alone or in combination, that is sufficient to kill the target insect, increase mortality, or inhibit the incidence, growth, development or reproduction of the target insect. Typically, a concentration range about $1 \times 10^7$ to about $1 \times 10^{10}$ colony forming units (CFU)/ml is effective including about $1 \times 10^7$, $2 \times 10^7$, $3 \times 10^7$ $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, or $1 \times 10^{11}$ or more CFU/ml is effective. The effective rate can be affected by insect species present, stage of insect growth, insect population density, and environmental factors such as temperature, wind velocity, rain, time of day and seasonality. The amount that will be within an effective range in a particular instance can be determined by laboratory or field tests.

III. Administration of Compositions Comprising Csp_P to Insects

An insect (e.g., an *Anopheles* or *Aedes* mosquito) can be exposed to a composition comprising Csp_P in combination with a delivery agent in any suitable manner that permits administering the composition to the insect. For example, the insect can be contacted with the composition in a pure or substantially pure form, for example a solution containing Csp_P. In a particular embodiment, the composition comprises Csp_P and a delivery agent. In another particular embodiment, the insect can be simply "soaked" or "sprayed" with a solution comprising Csp_P.

Alternatively, the composition comprising Csp_P can be linked to a food component of the insect, such as artificial nectar or sugar bait, for ease of delivery and/or in order to increase uptake of the composition by the insect. Methods for oral introduction include, for example, directly mixing a composition with the insect's food, spraying the composition in the insect's habitat or field including standing water areas. The composition can also be incorporated into the medium in which the insect grows, lives, reproduces, feeds, or infests.

In another embodiment, the composition is in the form of a bait. The bait is designed to lure the insect to come into contact with the composition. In one embodiment, upon coming into contact therewith, the composition is then internalized by the insect, by ingestion for example. The bait can depend on the species being targeted. An attractant can also be used. The attractant can be a pheromone, such as a male or female pheromone. The attractant acts to lure the insect to the bait, and can be targeted for a particular insect or can attract a whole range of insects. The bait can be in any suitable form, such as a solid, paste, pellet or powdered form.

The bait can also be carried away by the insect back to the colony. The bait can then act as a food source for other members of the colony, thus providing an effective control of a large number of insects and potentially an entire insect pest colony.

The baits can be provided in a suitable "housing" or "trap". Such housings and traps are commercially available and existing traps can be adapted to include the compositions of the invention. The housing or trap can be box-shaped for example, and can be provided in pre-formed condition or can be formed of foldable cardboard for example. Suitable materials for a housing or trap include plastics and cardboard, particularly corrugated cardboard. The inside surfaces of the traps can be lined with a sticky substance in order to restrict movement of the insect once inside the trap. The housing or trap can contain a suitable trough inside which can hold the bait in place. A trap is distinguished from a housing because the insect cannot readily leave a trap following entry, whereas a housing acts as a "feeding station" which provides the insect with a preferred environment in which they can feed and feel safe from predators.

In certain embodiments of the invention, an area can be treated with a composition of the present invention, for example, by using a spray formulation, such as an aerosol or a pump spray. In certain embodiments of the invention, an area can be treated, for example, via aerial delivery, by truck-mounted equipment, or the like. Of course, various treatment methods can be used without departing from the spirit and scope of the present invention. In some embodiments, the composition is sprayed by e.g., backpack spraying, aerial spraying, spraying/dusting etc.

In specific embodiment, treatment can include use of an oil-based formulation, a water-based formulation, a residual formulation, and the like. In some embodiments, combinations of formulations can be employed to achieve the benefits of different formulation types.

In further embodiments, the compositions and methods of the present invention can be used to control other insects. As used herein the term "insect" describes any insect, meaning any organism belonging to the Kingdom Animals, more specific to the Phylum Arthropoda, and to the Class Insecta or the Class Arachnida. In specific embodiments of the present invention, the insect can belong to the following orders: Acari, Araneae, Anoplura, Coleoptera, Collembola, Dermaptera, Dictyoptera, Diplura, Diptera, Embioptera, Ephemeroptera, Grylloblatodea, Hemiptera, Homoptera, Hymenoptera, Isoptera, Lepidoptera, Mallophaga, Mecoptera, Neuroptera, Odonata, Orthoptera, Phasmida, Plecoptera, Protura, Psocoptera, Siphonaptera, Siphunculata, Thysanura, Strepsiptera, Thysanoptera, Trichoptera, and Zoraptera.

As used herein, the terms "pest" or "insect pests" include but are not limited to the following examples: from the order Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp, *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia Nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.; from the order Coleoptera, for example, *Agriotes* spp., *Anthonomus* spp., *Atomaria linearis, Chaetocnema tibialis, Cosmopolites* spp., *Curculio* spp., *Dermestes* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.; from the order Orthoptera, for example, *Blatta* spp., *Blattella* spp., *Gryllotalpa* spp., *Leucophaea maderae, Locusta* spp., *Periplaneta* ssp., and *Schistocerca* spp.; from the order Isoptera, for spp; from the order Psocoptera, for spp.; from the order Anoplura, for example *jfaematopinus* spp., *Linognathus* spp., *Pediculus* spp., *Pemphigus* spp. and *Phylloxera* spp.; from the order Mallophaga, for example *Trichodectes* spp.; from the order Thysanoptera, for spp., *Hercinothrips* spp., *Taeniothrips* spp., *Thrips palmi, Thrips tabaci* and *Scirtothrips aurantii*; from the order Heteroptera, for example, *Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp., *Triatoma* spp., Miridae family spp. such as *Lygus hesperus* and *Lygus lineoloris*, LygaeidaQ family spp. such as *Blissus leucopterus*, and Pentatomidae family spp.; from the order Homoptera, for example, *Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lacanium comi, Lepidosaphes* spp., *Macrosiphus* spp., *Myzus* spp., *Nehotettix* spp., *Nilaparvata* spp., *Paratoria* spp., *Pemphigus* spp., *Planococcus* spp., *Pseudaulacaspis* spp., *Pseudococcus* spp., *Psylla* ssp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*; from the order Hymenoptera, for example, *Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* ssp.; from the order Diptera, for example, *Aedes* spp., *Anopheles* spp., *Antherigona soccata, Bibio hortulanus, CalHphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomysa* spp., *Lucilia* spp., *Melanagromyza* spp., *Musca* ssp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp., from the order Siphonaptera, for example, *Ceratophyllus* spp. and *Xenopsylla cheopis* and from the order Thysanura, for example *Lepisma* saccharin.

In other embodiments, a composition comprising Csp_P can be administered to an insect including, but not limited to, those with piercing-sucking mouthparts, as found in Hemiptera and some Hymenoptera and Diptera such as mosquitoes, bees, wasps, lice, fleas and ants, as well as members of the Arachnidae such as ticks and mites; order, class or family of Acarina (ticks and mites) e.g., representatives of the families Argasidae, Dermanyssidae, Ixodidae, Psoroptidae or Sarcoptidae and representatives of the species *Amblyomma* spp., *Anocentor* spp., *Argas* spp., *Boophilus* spp., *Cheyletiella* spp., *Chorioptes* spp., *Demodex* spp., *Dermacentor* spp., *Dermanyssus* spp., *Haemophysalis* spp., *Hyalomma* spp., *Ixodes* spp., *Lynxacarus* spp., *Mesostigmata* spp., *Notoedres* spp., *Omithodoros* spp., *Omithonyssus* spp., *Otobius* spp., *otodectes* spp., *Pneumonyssus* spp., *Psoroptes* spp., *Rhipicephalus* spp., *Sarcoptes* spp., or *Trombicula* spp.; Anoplura (sucking and biting lice) e.g., representatives of the species *Bovicola* spp., *Haematopinus* spp., *Linognathus* spp., *Menopon* spp., *Pediculus* spp., *Pemphigus* spp., *Phylloxera* spp., or *Solenopotes* spp.; Diptera (flies) e.g., representatives of the species *Aedes* spp., *Anopheles* spp., *Calliphora* spp., *Chrysomyia* spp., *Chrysops* spp., *Cochliomyia* spp., *Cw/ex* spp., *CuUcoides* spp., *Cuterebra* spp., *Dermatobia* spp., *Gastrophilus* spp., *Glossina* spp., *Haematobia* spp., *Haematopota* spp., *Hippobosca* spp., *Hypoderma* spp., *Lucilia* spp., *Lyperosia* spp., *Melophagus* spp., *Oestrus* spp., *Phaenicia* spp., *Phlebotomus* spp., *Phormia* spp., *Sarcophaga* spp., *Simulium* spp., *Stomoxys* spp., *Tabanus* spp., *Tannia* spp. or *Zzpu/alpha* spp.; Mallophaga (biting lice) e.g., representatives of the species *Damalina* spp., *Felicola* spp., *Heterodoxus* spp. or *Trichodectes* spp.; or Siphonaptera (wingless insects) e.g., representatives of the species *Ceratophyllus* spp., *Xenopsylla* spp; Cimicidae (true bugs) e.g., representatives of the species *Cimex* spp., *Tritominae* spp., *Rhodinius* spp., or *Triatoma* spp.

Embodiments of the present invention can be used to control parasites. As used herein, the term "parasite" includes parasites, such as but not limited to, protozoa, including intestinal protozoa, tissue protozoa, and blood protozoa. Examples of intestinal protozoa include, but are not limited to: *Entamoeba hystolytica, Giardia lamblia, Cryptosporidium muris*, and *Cryptosporidium parvum*. Examples of tissue protozoa include, but are not limited to: *Trypanosomatida gambiense, Trypanosomatida rhodesiense, Trypanosomatida crusi, Leishmania mexicana, Leishmania braziliensis, Leishmania tropica, Leishmania donovani, Toxoplasma gondii*, and *Trichomonas vaginalis*. Examples of blood protozoa include, but are not limited to *Plasmodium vivax, Plasmodium ovale, Plasmodium malariae*, and *Plasmodium falciparum. Histomonas meleagridis* is yet another example of a protozoan parasite.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: *Chromobacterium* Csp_P Reduces Malaria and Dengue Infection in Vector Mosquitoes The influence of the gut microbiota on the vector competence of disease vectors such as mosquitoes has gained increasing interest over the past decade. Previous work has shown that co-infection of *Anopheles* mosquitoes with *Plasmodium* and with *Serratia* sp. or *Enterobacter* sp. bacteria leads to reduced *Plasmodium* infection. Additionally, the presence of certain bacterial species in *Aedes* mosquito midguts leads to a lower intensity of dengue virus infection. Studies have also shown that *Anopheles* and *Aedes* mosquitoes that have had their gut microbiota experimentally reduced via antibiotic treatment show higher *Plasmodium* and dengue virus infection levels, respectively, than do their untreated counterparts. The anti-pathogen activity of mosquito midgut bacteria has been attributed to the elicitation of the mosquito immune system in some instances, and to direct anti pathogenic activity of bacteria-produced molecules in others. Activation of the immune deficiency (IMD) pathway, the major anti-*P. falciparum* immune pathway, has been shown to be mediated through an interaction between the pattern recognition receptor PGRP-LC and the midgut microbiota. In turn, microbe-derived anti-pathogen factors have been characterized in some microbe-host interaction systems and include cytotoxic metalloproteases, hemolysins, antibiotics, haemaglutinins, proteases, prodigiosin pigments, and iron chelators (siderophores).

In nature, bacteria commonly grow attached to surfaces in complex matrices of cells, proteins, polysaccharides, and DNA (biofilm growth), rather than as single free-swimming cells (planktonic growth). Biofilm formation allows the bacteria to survive exposure to host-derived antimicrobial factors and other environmental stressors. Furthermore, bacterial cells in a biofilm have quite different gene expression and metabolic profiles than do cells in a free-swimming planktonic state. Studies of *Pseudomonas aeruginosa* colonization of the *Drosophila melanogaster* gut have shown that biofilm formation can dramatically affect dissemination in the hemolymph and fly mortality.

In this study, we show that a *Chromobacterium* sp_Panamam isolate, Csp_P, isolated from the midgut of field-collected *Ae. aegypti* mosquitoes, exerts in vitro anti-*Plasmodium* and anti-dengue activity when grown under biofilm conditions. Csp_P can effectively colonize the intestines of the two most important mosquito disease vectors, *An. gambiae* and *Ae. aegypti*, where it blocks *Plasmodium* and dengue infection. It also exerts entomopathogenic activity against both larval and adult stages and could therefore be used for the development of a biocontrol agent. Csp_P's anti-pathogen activities appear to be mediated by stable secondary metabolites, suggesting that Csp_P is a source of potentially interesting candidates for the development of therapeutic and transmission-blocking drugs.

Materials and Methods

Ethics Statement.

This study was carried out in strict accordance with the recommendations in the Guide for the Care and Use of Laboratory Animals of the National Institutes of Health. Mice were only used for mosquito rearing as a blood source according to approved protocol. The protocol was approved by the Animal Care and Use Committee of the Johns Hopkins University (Permit Number: M006H300). Commercial anonymous human blood, supplied from Interstate Blood Bank Inc., was used for *Plasmodium* and dengue virus infection assays in mosquitoes, and informed consent was therefore not applicable. The Johns Hopkins School of Public Health Ethics Committee has approved this protocol. Mosquito collections were performed in residences after owners/residents permission.

Mosquito Rearing and Antibiotic Treatment.

*Aedes aegypti* mosquitoes were from the Rockefeller strain, and *Anopheles gambiae* mosquitoes were from the Keele strain. Both were maintainedonal 0% sugar solution at 27° C. and 95% humidity with a12-h light/dark cycle. Sterile cotton, filter paper, and sterilized nets were used to maintain the cages as sterilely as possible. For experiments utilizing aseptic mosquitoes, females were maintained on a 10% sucrose solution with 20 U penicillin and 20 µg streptomycin from the first day post-eclosion until 1-2 days prior to challenge. The effectiveness of the antimicrobial treatment was confirmed by colony forming unit assays prior to blood-feeding or bacterial challenge.

Introduction of Bacteria Via Sugar Meal.

In cases where mosquitoes were antibiotic treated, reintroduction of bacteria through a sugar meal was done by first treating mosquitoes with antibiotics for 2-3 days after emergence, then providing them with 10% sucrose (for *An. gambiae*) or sterile water (for *Ae. aegypti*) for 24 h post-antibiotic treatment. When mosquitoes were not antibiotic treated, they were maintained on 10% sucrose for 2-5 days post emergence. *Ae. aegypti* were given sterile water during the final 24 hours of this period. In all cases, mosquitoes were then starved overnight and fed for 24 h on cotton strips moistened with a 1.5% sucrose solution containing Csp_P at a final concentration of approximately $10^8$ CFU/ml for *An. gambiae* and $10^6$ CFU/ml for *Ae. aegypti*. In some experiments (FIGS. 1 and 2), *Ae. aegypti* mosquitoes were also fed Csp_P at a final concentration of $10^{10}$ CFU/ml.

Assaying Prevalence and Bacterial Load of Csp_P.

In antibiotic treated mosquitoes, midguts were dissected three days post ingestion of Csp_P, homogenized in 1×PBS and plated on LB agar. Colonies were then counted to estimate colony forming units (CFUs) per midgut as well as prevalence of Csp_P. In mosquitoes not treated with antibiotics, prevalence and/or bacterial load was estimated in one of two ways. For *An. gambiae*, midguts were dissected at one and two days post Csp_P ingestion, homogenized in 1×PBS and serial dilutions of the homogenate were plated on LB agar supplemented with ampicillin (10,000 ug/ml). Csp_P is highly resistant to ampicillin and grows readily even at this high concentration. We verified that Csp_P was the only bacterium growing on antibiotic treated plates by first confirming that all colonies that grew were similar in color, growth rate and colony morphology. 16s rDNA was then sequenced from a subset of colonies and verified to match the sequence of Csp_P from pure freezer stock.

It was not possible to use this method for *Ae. aegypti* because their midguts commonly contained other highly ampicillin-resistant bacteria. These contaminants grew to very high numbers on the ampicillin-treated plates and interfered with the detection of Csp_P. DNA was therefore extracted using the ZR Soil Microbe DNA MicroPrep kit (Zymo Research) from samples dissected 1 and 3 days after feeding on a sugar meal containing either PBS or Csp_P ($10^{10}$ CFU/ml). The manufacturer's protocol was altered in the following way: instead of using lysis buffer to disrupt cells, each midgut was put in 500 µl 1×PBS, 25 µl lysozyme (10 mg/ml) and 7.5 µl mutanolysin (10 KU/ml) were added and the samples were incubated at 37° C. for 1.5 h. 15 µl proteinase K and 25 µl 10% SDS were then added, samples were incubated at 55° C. for 1 h, and the standard protocol was then resumed. A diagnostic PCR was performed to assess the presence of Csp_P in each individual midgut. Primers were designed to amplify a 415 bp fragment of the Csp_P hydrogen cyanide synthase B gene and the primers were verified to be Csp_P-specific using Primer BLAST from NCBI (Forward primer: 5'AGGGCGTAACCCTGGACTAT 3' (SEQ ID NO:2), Reverse primer: 5' CCGAAGGAACTGGCTTCGTA 3' (SEQ ID NO:3)). PCR was performed with the above primers using 10 ng DNA as template and Phusion High-Fidelity DNA Polymerase according to the manufacturer's instructions, with the following exceptions: 0.5 µl of each primer (10 m) was used, and 0.25 µl BSA was added to each reaction. Cycling conditions were as follows: 95° C. for 30 seconds, [95° C. for 30 s, 65° C. for 30 s, 72° C. for 45 s]×27 cycles, 72° C. for 10 minutes. 8 µl of each sample was run on a 1% agarose gel and visualized at 400 ms exposure. A visible 415 bp band was considered positive evidence of Csp_P bacteria (data not shown). A very faint band was detected in one of 40 PBS samples, suggesting a minor contamination event or the presence of another bacterium with high sequence identity to Csp_P. This was an isolated incident and was not seen in any other PBS samples. Two independent PCR products were sequenced from Csp_P fed samples and verified to be a perfect match to the sequence obtained from Csp_P sequenced directly from freezer stock. To serve as a positive control and to allow estimation of the sensitivity of the diagnostic PCR, a standard curve was run in which a range of $10^7$-$10^1$ copies of the Csp_P hcn B PCR product was used as template. In this way, it was possible to estimate the minimum detection threshold of this assay. Using the above mentioned PCR conditions, a band was detectable in wells containing $10^3$ initial copies of the hcn B product but not in wells containing $10^2$ initial copies, suggesting that this assay is capable of detecting a minimum of $10^3$ copies of Csp_P/midgut.

Introduction of Bacteria Via Blood Meal.

At 2 days prior to blood feeding, sucrose was removed, and the mosquitoes were given sterile water. They were then starved for 12 h prior to blood feeding. Csp_P was grown overnight in liquid LB at 30° C. The overnight culture (1 ml) was then pelleted, washed with 1×PBS, and resuspended in 1×PBS to OD600=1.0, which equals a concentration of approximately $10^8$ CFU/m. Mosquitoes were then allowed to membrane-feed on blood containing bacteria or IX PBS as a control (blood mixture: 50% 1.0 OD600 bacterial culture or IX PBS, 40% blood, 10% human serum). Bacteria-fed adult females ingested approximately $10^5$ CFU per mosquito.

Exposure of Larvae to Csp_P.

At 2-4 days post-hatching, larvae were placed in cell culture plates in groups of 10 per well. Each well contained 5 ml sterile water plus a small amount of larval food (liver powder, tropical fish flake food, and rabbit food pellets mixed in a 2:1:1 ratio). We then added 50 µl of an overnight culture of Csp_P diluted to OD600=1.0 ($10^8$ CFU/ml) to each well; IX PBS was added to control wells, and mortality was monitored in all wells for a 5 day period.

Cell Culture Maintenance, Mosquito Infections with Dengue Virus, and Titration of Infected Midgets.

Dengue virus serotype 2 (New Guinea C strain, DENV-2) was propagated in the C6/36 mosquito cell line according to previously published methods. In brief, cell line infection was allowed to proceed for 5-7 days, at which time the cells were harvested with a cell scraper and lysed by freezing and thawing in dry CO2 and a 37° C. water bath, then centrifuged at 800 g for 10 min. Dengue virus serotype 2 was isolated and mixed 1:1 with commercial human blood and used for infections as described in. Mosquitoes that had previously fed on Csp_P bacteria-sucrose solution were starved overnight prior to dengue virus infection. Infected mosquitoes were collected at 7 days post-infection and surface-sterilized by dipping them in 70% ethanol for 1 min and then rinsing them twice in IX PBS for 2 min each. Midgut dissection was done in one drop of 1×PBS under sterile conditions, and the midgut was transferred to a microcentrifuge tube containing 150 µl of MEM. Midguts were homogenized using a Kontes pellet pestle motor, filtered, and stored at −80° C. until ready for virus titration.

Dengue virus titration of infected midguts was done as previously reported. In brief, the infected midgut homogenates were serially diluted and inoculated into C6/36 cells in 24-well plates. After an incubation of 5 days at 32° C. and 5% CO2, the plates were fixed with 50%/50% methanol/acetone, and plaques were assayed by peroxidase immunostaining using mouse hyperimmune ascitic fluid specific for DENV-2 as the primary antibody and a goat anti-mouse HRP conjugate as the secondary antibody. In addition, where indicated, dengue virus plaque assays were conducted in BHK-21 cells. At 5 days post-infection, the 24-well plates were fixed and stained with crystal violet. Plaques (formed by cells with cytopathic effect) were counted and analyzed.

*P. falciparum* Cultivation, Mosquito Infections, and Oocyst Counts.

*P. falciparum* strain NF54 was maintained in continuous culture according to the method described by Tragger and Jensen, 192 SCIENCE 673-75 (1976). In brief, *P. falciparum* was grown in O+ red blood cells (RBCs) at 2% hematocrit and RPMI 1640 medium supplemented with glutamine, HEPES, hypoxanthine, and 10% O+ human serum. To maintain a microaerophilic environment, parasites were maintained in a candle jar at 37° C. Use of human erythrocytes to support the growth of *P. falciparum* was approved by the internal review board of the Bloomberg School of Public Health. Gametocytemia and exflagellation events were assessed after 18 days of *P. falciparum* culture. The gametocyte culture was centrifuged and diluted in a mixture of RBCs supplemented with serum. Mosquitoes were rendered aseptic via antibiotic treatment and then fed on membrane feeders for 30 min with blood containing *P. falciparum* gametocytes. Csp_P was either added directly to the infectious blood meal (bacterial concentration=$10^6$ CFU/mL) or introduced via sugar meal as described above 3 to 4 days prior to the infectious blood meal. On the same day as the blood meal, mosquitoes were sorted, and the unfed mosquitoes were removed. At 7 to 8 days after blood feeding, the fed mosquitoes were dissected, and their midguts were stained with 0.1% mercurochrome. The number of oocysts per midgut was determined with a light contrast microscope, and the median was calculated for the control and each experimental condition. More than three independent replicates were used per group.

Csp_P Culture Preparations for In Vitro Anti-*Plasmodium* and Anti-Dengue Activity Assays.

To grow bacteria in planktonic conditions, we spiked 5 ml sterile LB with 5 µl of bacterial freezer stock and allowed the culture to grow overnight at 30° C. with shaking. We then diluted planktonic cultures to OD600=1.0 (+0.1) with additional sterile LB broth which, for Csp_P, results in a concentration of approximately $10^8$ CFU/ml. To grow bacteria under biofilm conditions, we dispensed 1 ml of sterile LB into each well of a 24-well cell culture plate and spiked each well with 1 µl of bacterial freezer stock. We then allowed the culture to grow at room temperature without shaking for 48 h. Csp_P biofilm supernatant was harvested from single bacterial culture wells containing 48-h biofilm and was found to have an average bacterial concentration of approximately $10^9$ CFU/ml. To harvest fresh biofilm, we removed the supernatant from five wells containing 48-h biofilm, resuspended the biofilm from each well in 100 µl 1×PBS and pooled the five wells. For Csp_P, this pooled biofilm solution contained approximately $10^9$ CFU/ml and an average of 5 mg of biofilm (dry weight). To obtain desiccated biofilm, we collected the fresh biofilm from five wells as indicated, centrifuged the biofilm at 5000 rpm for 2.5 min, removed the PBS supernatant, and allowed the biofilm to dry at room temperature. On the day of the experiment, we resuspended the five wells of desiccated biofilm in 500 µl 1×PBS to mimic the fresh biofilm treatment. To heat-inactivate the fresh biofilm, we collected fresh biofilm as indicated and incubated samples at 90° C. for 24 h prior to the experiment.

In Vitro Anti-*Plasmodium* Activity Assays.

Figure 13:
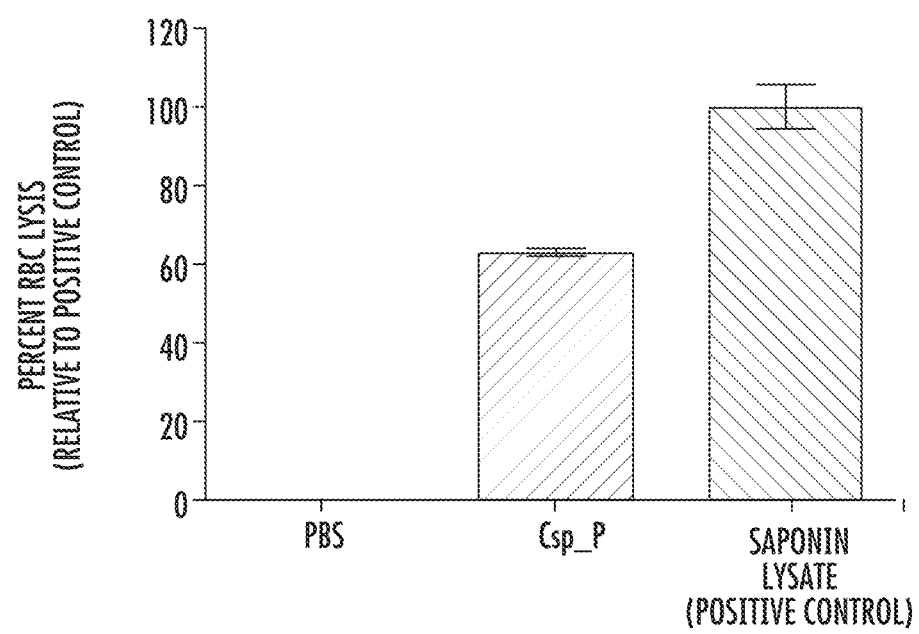
FIG. 13. Csp_P biofilm is hemolytic when exposed to human red blood cells. We mixed filtered Csp_P fresh biofilm with human erythrocytes, incubated 24 h at 37° C. and centrifuged at 2000 rpm for 5 min. We then removed the supernatant and assayed absorbance at 405 nm in an ELISA plate reader (HTS 7000 Perkin Elmer). 1×PBS was used as a negative control and saponin as a positive control.

We prepared Csp_P bacterial cultures as described above and filtered all samples through a 0.2-µm filter. Asexual-stage assay: Inhibition of asexual-stage *P. falciparum* was assessed using a SYBR green I-based fluorescence assay as described earlier. Csp_P biofilm was grown for 36 h for this experiment because 48-h biofilm causes hemolysis of RBCs (FIG. 13), which interferes with the assay. Parasites were synchronized using 5% sorbitol; 5 µl of each bacterial preparation was dispensed in triplicate wells of 96-well microplates, followed by addition of 95 µl of synchronous ring-stage *P. falciparum* cultures at 1% hematocrit and 1% parasitemia. Chloroquine (250 nM) was used as a positive control, and parasite growth medium was used as a negative control. After 72 h of incubation in a candle jar at 37° C., an equal volume of SYBR green-I solution in lysis buffer (Tris [20 mM; pH 7.5], EDTA [5 mM], saponin [0.008%; w/v], and Triton X-100 [0.08%; v/v]) was added to each well and mixed gently, then incubated 1-2 h in the dark at room temperature. Plates were read on a fluorescence plate reader (HTS 7000, Perkin Elmer), with excitation and emission wavelengths of 485 and 535 nm, respectively. Percent inhibition was calculated relative to negative (0% inhibition) and positive controls (100% inhibition). Three biological replicates were assayed.

Ookinete-Stage Assay:

To assess inhibition of ookinete-stage *P. berghei* parasites, female Swiss Webster mice (6-8 weeks old) were infected with a transgenic strain of *P. berghei* that expresses *Renilla* luciferase. Starting at 3 days post-infection, exflagellation assays were performed until at least 20 exflagellation events were recorded in a 20× field. At this time, mice were bled by heart puncture using a heparinized needle, and the blood was diluted in 10 volumes of ookinete medium (RPMI 1640, 10% FBS, 50 mg/ml hypoxanthine, and 2 mg/ml $NaHC0^3$, pH 8.3) with 4% mouse RBC lysate. Samples (50 µl) of each bacterial preparation were then mixed with the infected blood and incubated for 24 h at 19° C. Ookinete counts were determined using the *Renilla* luciferase assay system (Promega, USA) according to the manufacturer's instructions. The experiment was performed on two independent days, and each sample was assayed in triplicate on each day.

Gametocyte-Stage Assay:

Inhibition of gametocyte-stage *P. falciparum* by Csp_P was assessed as described previously. To prevent hemolysis of RBCs, Csp_P biofilm was grown for 36 and 42 hours for this experiment. In brief, NF54 *P. falciparum* cultures were started at 0.5% asexual parasitemia and 4% hematocrit. Csp_P bacterial preparations were added 15 days after *Plasmodium* cultures were initiated, and gametocytemia was determined 18 days after culture initiation. At least three biological replicates were tested for each culture preparation. More than 500 erythrocytes were examined for gametocytes across Giemsa-stained blood films from each sample.

In Vitro Anti-Dengue Activity Assays.

We prepared Csp_P bacterial cultures as described above (planktonic state, biofilm, biofilm supernatant, desiccated biofilm, and heat-inactivated biofilm), mixed 75 µl of each bacterial culture preparation with 75 µl of MEM containing dengue virus serotype 2 and incubated the mixture at room temperature for 45 min. Samples were then filtered through a 0.2-µm filter, serially diluted, and used to infect BHK21-15 cells. Plaque assays were conducted as described above to assess dengue virus infectivity. Percent inhibition was calculated as the percent decrease in PFU/ml relative to the PBS+LB control, which was standardized to 0% inhibition. The experiment was performed on two independent days, and each assay was performed in triplicate on each day. In experiments in which dengue was mixed with human blood before exposure to Csp_P, bacterial biofilms were not removed from the cell culture plate. Rather, dengue virus was mixed 1:1 with human blood, and 150 µl of this mixture was added directly to each well containing Csp_P biofilm and incubated for 45 min at 30° C. Following this incubation period, the blood-dengue virus solution was mixed with the biofilm, and 50 µl of the mixture was then drawn from the well, diluted in MEM, and filtered through a 0.2-µm filter. The resulting filtrate solution was then serially diluted and used to infect C6/36 cells.

Assay for Sequestration of Viral Particles by Csp_P Biofilm.

To assess whether the antidengue activity of Csp_P was due to sequestration of DENV by the Csp_P biofilm, we mixed a dengue virus suspension with Csp_P 48 hr biofilm or LB broth and incubated it for a period of 45 min. Samples were then centrifuged at 5,000 rpm for 5 min. The supernatants were collected, and RNA was extracted from equal volumes (50 µl) of experimental (biofilm+DENV) and control (LB+DENV) samples using the RNeasy kit (Qiagen). Comparison of viral RNA loads in the extracted supernatant was done via RT-qPCR relative quantification, using 2 µl of the viral RNA in a 20-µl reaction volume.

Assessing pH Effects on Dengue Virus Infectivity.

The pH of bacterial biofilms and supernatants was assessed with a micro-pH electrode (Lazar Lab) at room temperature. Effects of pH changes on dengue virus infectivity were assessed by adjusting the pH of the MEM with NaOH and HCl until the desired range of pH values was obtained: 5.0, 7.7, 8.5, and 10.0. The pH-adjusted MEM was then mixed with dengue virus-laden blood and incubated for 45 min prior to serial dilution and infection of C6/36 cells.

Cell Viability Assays.

Cell viability assays on the mosquito cell line C6/36 and the vertebrate cell line BHK-21 were performed via trypan blue staining (0.4%, Invitrogen) according to the manufacturer's instructions. In brief, 50 µl of suspended cells were placed in a microcentrifuge tube and mixed with 10 µl of Csp_P filtered fresh biofilm or PBS as a control. C6/36 cells were incubated at 32° C. and BHK-21 cells were incubated at 37° C.+5% C02 for 45 min. Cells were then mixed with 12 µl of 0.4% trypan blue stain. The mixture was allowed to stand for 5 min at room temperature and then loaded into a hemocytometer for cell viability assessment and counting under a microscope.

Assay of the Effects of Csp_P Biofilm on Host Cell Susceptibility to DENV.

To assess whether exposure to Csp_P biofilm changes the susceptibility of the host cell to DENV, we conducted assays exposing C6/36 cells to Csp_P-filtered biofilm prior to dengue virus infection. Cells were grown to 80% confluency; the cell medium was then removed, washed once with 1×PBS, and then overlaid with 100 µl of Csp_P biofilm that had been filtered using a 2-µm filter or with 1×PBS (control) for about 10 min. Plates were then washed three times with 1×PBS and then infected with 100 µl of dengue virus for about 45 min. Cells were assessed for plaque formation at 6 days post-infection.

Hemolysis Assay.

Human erythrocytes were washed with RPMI 1640 medium until the supernatant was visually free of hemoglobin pigment. The washed erythrocytes were suspended in malaria complete medium to yield a 1% hematocrit. Filtered Csp_P biofilm was mixed with erythrocytes and incubated up to 24 h at 37° C. To separate lysed RBC cytosol from whole RBCs, the suspension was centrifuged at 2000 rpm for 5 min. The resulting supernatant was carefully aspirated and plated in new 96-well microplates. Control erythrocytes without any bacterial material were used as a negative control (blank), and freeze-thawed erythrocyte lysate was used as positive control (100% hemolysate). To determine the % lysis in test samples, plates were read at 405 nm in an ELISA plate reader (HTS 7000 Perkin Elmer), and the reading was expressed as a fraction of the positive control.

Real-time qPCR assays. To conduct real-time PCR assays, RNA samples were treated with Turbo DNase (Ambion, Austin, Tex., United States) and reverse-transcribed using M-MLV Reverse Transcriptase (Promega, USA). The real-time PCR assays were performed using the SYBR Green PCR Master Mix Kit (Applied Biosystems, Foster City, Calif., USA) in a 20-µl reaction volume; all samples were tested in duplicate. The ribosomal protein S7 gene was used for normalization of cDNA templates. Primer sequences used in these assays are given in Table 1.

TABLE 1

List of gene primers used in gene expression analyses of mosquito tissues post-bacterial challenge.

| Species | Gene Name | Sequence |
| --- | --- | --- |
| Aedes aegypti | Ribosomal S7 | Forward: 5'-GGGACAAATCGGCCAGGCTATC-3' (SEQ ID NO: 4)<br>Reverse: 5'-TCGTGGACGCTTCTGCTTGTTG-3' (SEQ ID NO: 5) |
| | Defensin-C | Forward: 5'-TTGTTTGCTTCGTTGCTCTTT-3' (SEQ ID NO: 6)<br>Reverse: 5'-ATCTCCTACACCGAACCCACT-3' (SEQ ID NO: 7) |
| | Cecropin-G | Forward: 5'-CCAAGCCTTGTGAACCAGTA-3' (SEQ ID NO: 8)<br>Reverse: 5'-GGCCACCTGCTTCAGACT-3' (SEQ ID NO: 9) |
| | Cecropin-E | Forward: 5'-CGAAGCCGGTGGTCTGAAG-3' (SEQ ID NO: 10)<br>Reverse: 5'-ACTACGGGAAGTGCTTTCTCA-3' (SEQ ID NO: 11) |
| | Lysozyme C | Forward: 5'-CCACGGCAACTGGATATGTCT-3' (SEQ ID NO: 12)<br>Reverse: 5'-TCTGCGTCACCTTGGTGGTAT-3' (SEQ ID NO: 13) |
| Anopheles gambiae | PGRP-LC | Forward: 5'-AGAATACCACACTAAGGCACAGT-3' (SEQ ID NO: 14)<br>Reverse: 5'-AGACTTACGATCCTGGTAAATGT-3' (SEQ ID NO: 15) |
| | Cecropin 1 | Forward: 5'-CCAGAGACCAACCAACCACCAA-3' (SEQ ID NO: 16)<br>Reverse: 5'-GCACTGCCAGCACGACAAAGA-3' (SEQ ID NO: 17) |

TABLE 1-continued

List of gene primers used in gene expression analyses
of mosquito tissues post-bacterial challenge.

| Species | Gene Name | Sequence |
|---|---|---|
| | FBN9 | Forward: 5'-CCAAGATGTCGGGCAAGTAT-3' (SEQ ID NO: 18)<br>Reverse: 5'-TTGTGGTACGTCAGCGAGTC-3' (SEQ ID NO: 19) |
| | TEP 1 | Forward: 5'-ATGCTCTGCTGTCGTTTGTG-3' (SEQ ID NO: 20)<br>Reverse: 5'-TTCGTGTCCTCCGGTATTTC-3' (SEQ ID NO: 21) |
| | LRRD7 | Forward: 5'-TCGGTGAGCAACAGTTTGA-3' (SEQ ID NO: 22)<br>Reverse: 5'-CTTCATTCCCGCTAATGCT-3' (SEQ ID NO: 23) |
| | Defensin 1 | Forward: 5'-GCGGTTCCAAAGTTCCGACA-3' (SEQ ID NO: 24)<br>Reverse: 5'-AGCGGGACACAAAATTGTTC-3' (SEQ ID NO: 25) |
| | Rel2 | Forward: 5'-CGGAGAAGTCGAAGAAAACG-3' (SEQ ID NO: 26)<br>Reverse: 5'-CACAGGCACACCTGATTGAG-3' (SEQ ID NO: 27) |

Statistical Analysis.

The Mann-Whitney U test, one-way ANOVA with Dunnett's post-test and pairwise Log-Rank tests for survival analysis were conducted using the GraphPad Prism statistical software package (Prism 5.05; GraphPad Software, Inc., San Diego, Calif.). Data in FIG. 5 were analyzed using an ANOVA, followed by a Tukey's test in R (R Foundation for Statistical Computing).

Results and Discussion

In a previous study, we isolated a Gram-negative bacterium Chromobacterium sp_Panamam (Csp_P) from the midgut of field-collected Ae. aegypti mosquitoes in Panama. The genus Chromobacterium spp. represents soil- and water-associated bacteria of tropical and subtropical regions, and members of this genus are known to produce a variety of bioactive compounds and to form biofilms. The most extensively studied member, Chromobacterium violaceum, has been found to produce violacein, a violet pigment compound with potent antimicrobial, antiparasitic, and tumoricidal activity. Csp_P can be cultured in Luria Bertani (LB) broth and on LB agar, on which it forms flat colonies with a tan color that become darker with time and are opaque when exposed to light. Csp_P does not produce violacein, but molecular characterization of its 16s rRNA gene sequence and phylogenetic analysis showed a 98% similarity to Chromobacterium haemolyticum and Chromobacterium aquaticum, probably its two closest relatives.

Csp_P Colonization of the Mosquito Midgut.

To assess the ability of Csp_P to colonize the mosquito midgut, we exposed antibiotic-treated mosquitoes to a sugar source containing $10^6$ colony forming units (CFU)/ml for Ae. aegypti or $10^8$ CFU/ml for An. gambiae for 24 h and then dissected, homogenized and plated the midguts on LB agar plates at 3 days post-exposure. Treatment with antibiotics through the sugar meal was performed to remove the native microbial flora which can fluctuate in terms of load and species composition between individual mosquitoes of the same cage and generation, thereby complicating the interpretation of our data. The presence of the native microbiota would also render it difficult to discriminate the Csp_P colonies from those of other species through visual inspection. Csp_P displayed an exceptional ability to rapidly colonize mosquito midguts, showing a prevalence of 80% in An. gambiae and 97% in Ae. aegypti cage populations at 3 days after exposure (FIG. 1A). Average bacterial loads at this time point were approximately $10^5$ and $10^4$ CFU per midgut in Ae. aegypti (FIG. 1B) and An. gambiae (FIG. 1C) females, respectively.

We also tested the ability of Csp_P to colonize the midguts of non-antibiotic treated mosquitoes. Because nearly all septic (i.e., non-antibiotic treated) An. gambiae mosquitoes had died two days after Csp_P introduction through sugar-feeding at $10^8$ CFU/ml (FIG. 2C), we were only able to assay prevalence and bacterial load of Csp_P at days one and two post feeding. At one day after Csp_P ingestion, we found that Csp_P was present in all sampled mosquitoes with an average bacterial load of $5.12 \times 10^4$ (FIG. 1D,E). At two days after Csp_P exposure, only 5% of Csp_P-fed An. gambiae were still alive (FIG. 2C) and Csp_P was detected in only one (12.5%) of these remaining mosquitoes (FIG. 1D, E). In septic Ae. aegypti mosquitoes that had fed on a $10^{10}$ CFU/ml Csp_P-containing sugar solution, we identified Csp_P in 79% of mosquitoes sampled on day 1 post feeding (FIG. 1F). At three days after feeding on the Csp_P containing sugar solution, approximately 30% of the Ae. aegypti were still alive (FIG. 2D) and Csp_P was detected in 15% of these mosquitoes (FIG. 1F). These data suggest that Csp_P colonized the vast majority of An. gambiae and Ae. aegypti mosquitoes by day 1 post exposure and that Csp_P caused rapid mortality in most individuals. The small percentage that survived up to day 2 or 3, post exposure, may have received a small dose of bacteria and succeeded in clearing it by the time they were dissected. It is difficult to compare the colonization efficiency between septic and antibiotic treated mosquitoes because the survival curves differ dramatically (FIG. 2). While it appears that Csp_P was better at colonizing the midgut of antibiotic treated *An. gambiae* (FIG. 1A vs. 1D) and *Ae. aegypti* (FIG. 1A vs. 1F), our measurement does not take into account that individuals died much more rapidly in the septic population. This rapid mortality likely selected for mostly Csp_P negative individuals by day 2 and 3 post-feeding.

Csp_P Exerts Entomopathogenic Activity Upon Mosquito Ingestion and Larval Exposure.

Figure 2C:
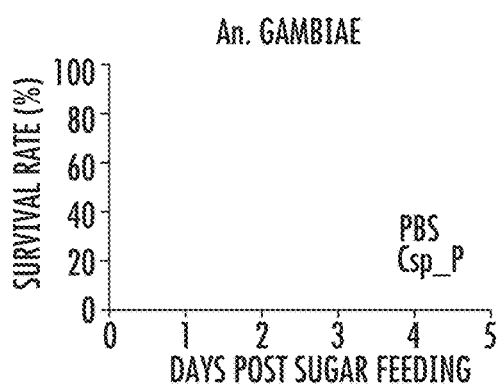
Figure 2D:
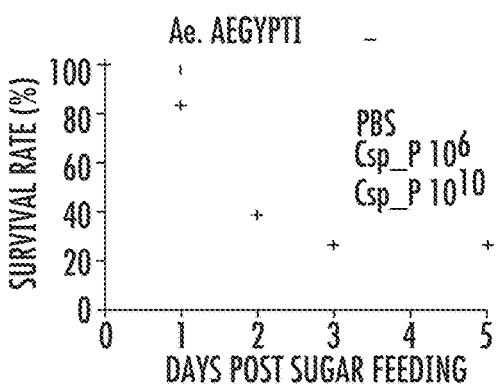
Figure 2E:
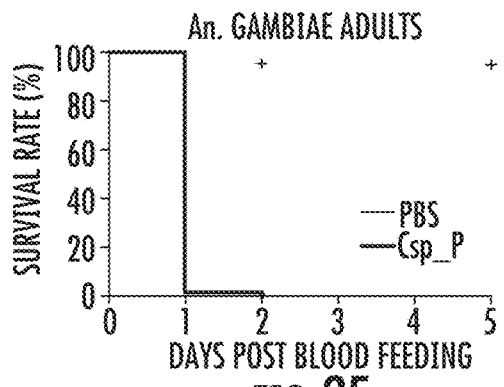
Figure 2F:
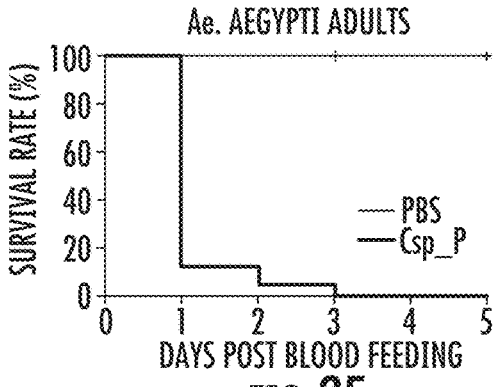

We examined the influence of Csp_P midgut colonization on mosquito longevity by exposing antibiotic-treated *An. gambiae* and *Ae. aegypti* mosquitoes to a sugar source for 24 h containing Csp_P at a final concentration of $10^8$ and $10^6$ CFU/ml, respectively, and then monitoring survival. This treatment led to a decrease in the longevity of both species when compared to non-exposed control mosquitoes (FIG. 2A, B). We repeated this experiment with septic (i. e., not antibiotic treated) *An. gambiae* and *Ae. aegypti*. We found that feeding on a sugar source containing Csp_P at a concentration of $10^8$ CFU/ml resulted in rapid mortality of *An. gambiae* adult females (FIG. 2C). Mortality of septic *Ae. aegypti* females was not increased after feeding on a sugar source containing Csp_P at a concentration of $10^6$ CFU/ml but was dramatically increased when the sugar meal contained Csp_P at a concentration of $10^{10}$ CFU/ml (FIG. 2D). These data suggest that Csp_P has strong entomopathogenic activity regardless of whether other microbes are present in the mosquito gut. We observed lower survival in septic *An. gambiae* and *Ae. aegytpi* after feeding on a blood meal containing Csp_P at a final concentration of $10^8$ CFU/ml (FIG. 2E, F). The stronger entomopathogenic effect upon Csp_P introduction through the blood meal was most likely because the mosquitoes received a large single bacterial dose upon bloodfeeding rather than the multiple low doses that would be expected during sugar feeding. It is also possible that Csp_P proliferated to high numbers in the nutritious blood.

Figure 2G:
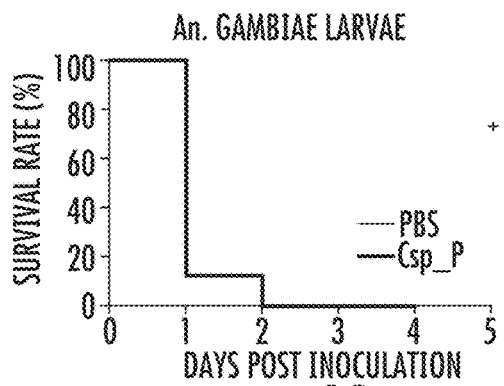
Figure 2H:
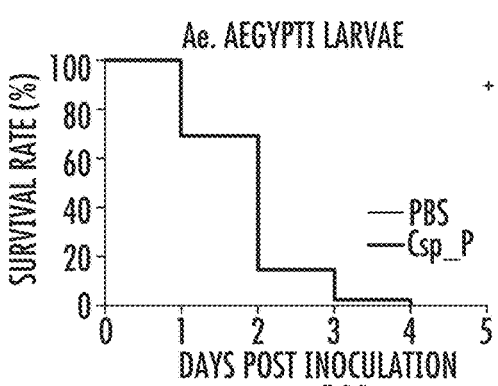

To study the influence of Csp_P on larval viability, we placed 2- to 4-day-old mosquito larvae in groups of 10 in pools containing 5 ml distilled water supplemented with 50 µl of a 1.0 OD600 liquid culture of Csp_P, and then monitored survival. This resulted in almost complete mortality of *An. gambiae* and *Ae. aegypti* larvae over a 3- and 2-day period, respectively, when compared to the control larvae that were exposed to the normal breeding water microbiota (FIG. 2G, H). These studies suggest that Csp_P-mediated mortality may be the direct result of a mosquitocidal factor or systemic infection through dissemination into the hemolymph; alternatively, its colonization of the midgut (or other tissues) might cause mortality indirectly by interfering with vital functions of the mosquito. Studies of *Pseudomonas aeruginosa* colonization of the *Drosophila melanogaster* gut have shown that biofilm formation can dramatically affect both dissemination within the hemolymph and fly mortality. Csp_P is capable of forming biofilms in vitro, though whether biofilm formation occurs within the mosquito midgut remains untested. *C. violaceum* produces cyanide at high cell density via the cyanide-producing hcnABC operon, a behavior that is reportedly regulated by quorum sensing. Cyanide production by bacteria has been shown to cause host mortality in both nematodes and insects. *Chromobacterium subtsugae* has previously been shown to exert oral toxicity in various insects of agricultural importance, but not in *Culex* mosquitoes.

Csp_P Colonization of the Mosquito Midgut Compromises Pathogen Infection.

To investigate whether the presence of Csp_P in the mosquito midgut could influence the infection of *An. gambiae* with *P. falciparum* and of *Ae. aegypti* with the dengue virus DENV2, we assayed the infection of mosquitoes that had been exposed to Csp_P through sugar feeding 2 days prior to feeding on parasite- or virus-infected blood. Approximately one week after *An. gambiae* had fed on a *P. falciparum* gametocyte culture, parasite infection was assayed by counting oocyst-stage parasites on the basal side of the mosquito midgut. DENV2 infection of the midgut of *Ae. aegypti* was assayed through standard plaque assays 7 days after an infectious bloodmeal. All experiments were initiated using similar numbers of adult females for each treatment, but because Csp_P exposure causes high mortality in adults (FIG. 2), very few Csp_P-fed mosquitoes were still alive when the parasite and dengue infection assays were conducted. Nevertheless, we found that surviving mosquitoes exposed to Csp_P through sugar feeding prior to feeding on infectious blood displayed significantly increased resistance to *P. falciparum* infection and DENV infection (FIG. 3). The inhibition of *P. falciparum* infection was even greater when Csp_P was introduced through the gametocyte-containing blood meal at $10^6$ CFU/ml (FIG. 3B), an effect most likely attributable to the larger number of ingested bacteria. Csp_P may inhibit pathogen infection directly through physical interaction with the pathogens or the production of anti-pathogen molecules. Alternatively, Csp_P may indirectly inhibit *Plasmodium* or dengue by (a) altering the long-term physiology or health of the mosquito such that pathogen infection is inhibited, (b) triggering a mosquito anti-pathogen response or (c) selecting for individuals that are more fit to resist Csp_P as well as DENV and *Plasmodium* infection. However, Csp_P's in vitro anti-pathogen activity (discussed below) suggests it has the potential to directly inhibit pathogen survival in the mosquito gut. Further studies are necessary to elucidate the mechanism by which Csp_P inhibits the pathogens in vitro and in vivo.

Csp_P Induces Mosquito Innate Immune System Genes.

Figure 7A:
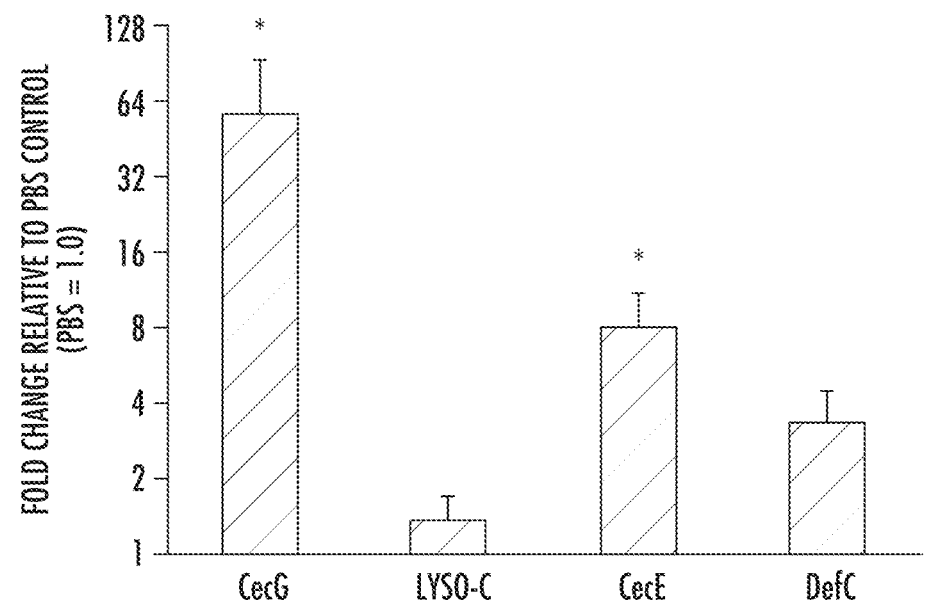
FIG. 7A-7B. Csp_P elicits immune gene expression in the mosquito midgut. Changes in the abundance of immune effector gene transcripts in the midgut of (FIG. 7A) *Ae. aegypti* and (FIG. 7B) *An. gambiae* mosquitoes were measured after the introduction of Csp_P via a sugar meal. For each gene, PBS controls were standardized to a value of 1.0, and Csp_P-induced changes in gene expression are shown as-fold change above or below PBS-fed controls. CecG=cecropin G, DefC=defensin C, LysC=lysozyme C, CecE=cecropin E, Cec1=cecropin 1, Def1=defensin 1, PGRP-LC=peptidoglycan recognition receptor LC, Rel2=Relish-like NF-κB transcription factor 2, Tep1=thioester protein 1, LRRD7=leucine-rich repeat domain protein 7 (a.k.a., APL2 and LRIM17), FBN9=fibronectin 9. Mann Whitney Tests comparing deltaCT values between bacteria-fed and PBS-fed mosquitoes for each gene were performed to determine significance (*, p<0.05).
Figure 7B:
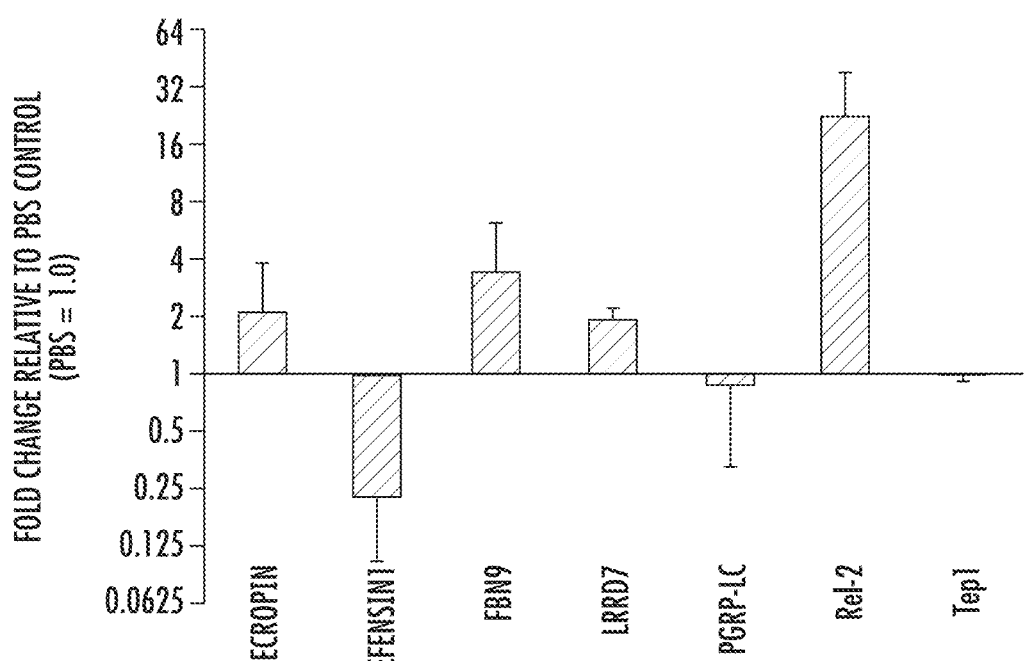

We have previously shown that the *An. gambiae* and *Ae. aegypti* midgut microbiota elicit basal immune activity by elevating the expression of several immune factors, including antimicrobial peptides and antipathogen factors. To determine Csp_P's potency in inducing the mosquito's innate immune system, we exposed mosquito SUA-5B cells to various concentrations of Csp_P and assayed for changes in the activity of a Cecropin1 promoter driving the expression of a luciferase reporter gene. We exposed these same cells to *Pseudomonas putida*, a Gram-negative bacterium that belongs to a bacterial genus commonly found in mosquito midguts. This experiment showed that Cec1 expression increased with increasing Csp_P exposure, providing evidence that Csp_P is a potent immune elicitor (FIG. 4). We also compared the transcript abundance of mosquito immune genes in midguts from antibiotic-treated naïve mosquitoes to those from mosquitoes that had been provided a sugar source spiked with Csp_P ($10^8$ CFU/ml for *An. gambiae* and $10^6$ CFU/ml for *Ae. aegypti*) 2 days earlier. We chose to assay gene expression at 2 days post exposure because this is the time at which increased mortality due to infection begins to occur. We hypothesized that infection levels and therefore any potential immune response would be high at this time. In *Ae. aegypti*, we found that cecropin E and G and defensin C displayed at least a 2-fold increase in transcript abundance in the midgut of *Ae. aegypti* colonized with Csp_P bacteria when compared to naïve controls (FIG. 7A). In *An. gambiae*, we found non-significant trends toward increased transcript abundance of the Rel2, FBN9 and cecropin genes and toward decreased transcript abundance of the defensin gene in the midgut tissue (FIG. 7B). These data represent a single time point post-infection, and while it is possible that additional time points may reveal dynamic patterns of Csp_P-induced changes in gene expression, our results generally agree with the cell culture data, and as a whole show that Csp_P has an immune-eliciting capacity in the mosquito gut.

Csp_P Inhibits *Plasmodium* Development and Abolishes Dengue Virus Infectivity in Vitro, Independent of the Mosquito.

To test whether Csp_P could exert a direct anti-*Plasmodium* or anti-dengue effect in vitro that is independent of the mosquito, we performed experiments in which parasite development and virus infectivity were assayed after exposure to various preparations of either planktonic or biofilm cultures of Csp_P. Planktonic-state Csp_P was obtained by culturing Csp_P in liquid LB at 30° C. overnight on a platform shaker. Biofilm was produced by culturing Csp_P in LB without agitation in a polystyrene 24-well plate at room temperature for 48 h, unless otherwise indicated. The anti-dengue and anti-*Plasmodium* activity of the following five different preparations of Csp_P was then tested: (a) 1 ml ($10^8$ CFU/ml) planktonic-state liquid culture, (b) 1 ml ($10^9$ CFU/ml) biofilm supernatant consisting of liquid LB drawn off freshly cultured biofilm, (c) 5 mg ($10^9$ CFU/ml) fresh biofilm resuspended in 1×PBS, (d) 5 mg desiccated biofilm prepared from biofilm collected 1-2 days prior to assay and allowed to completely desiccate at room temperature and then rehydrated in 1×PBS, (e) 5 mg heat-inactivated biofilm prepared by heating biofilm at 90° C. for 24 h, collected 1 day prior to assay.

Figures 5A, 5B, 5C, 5D, 5E:
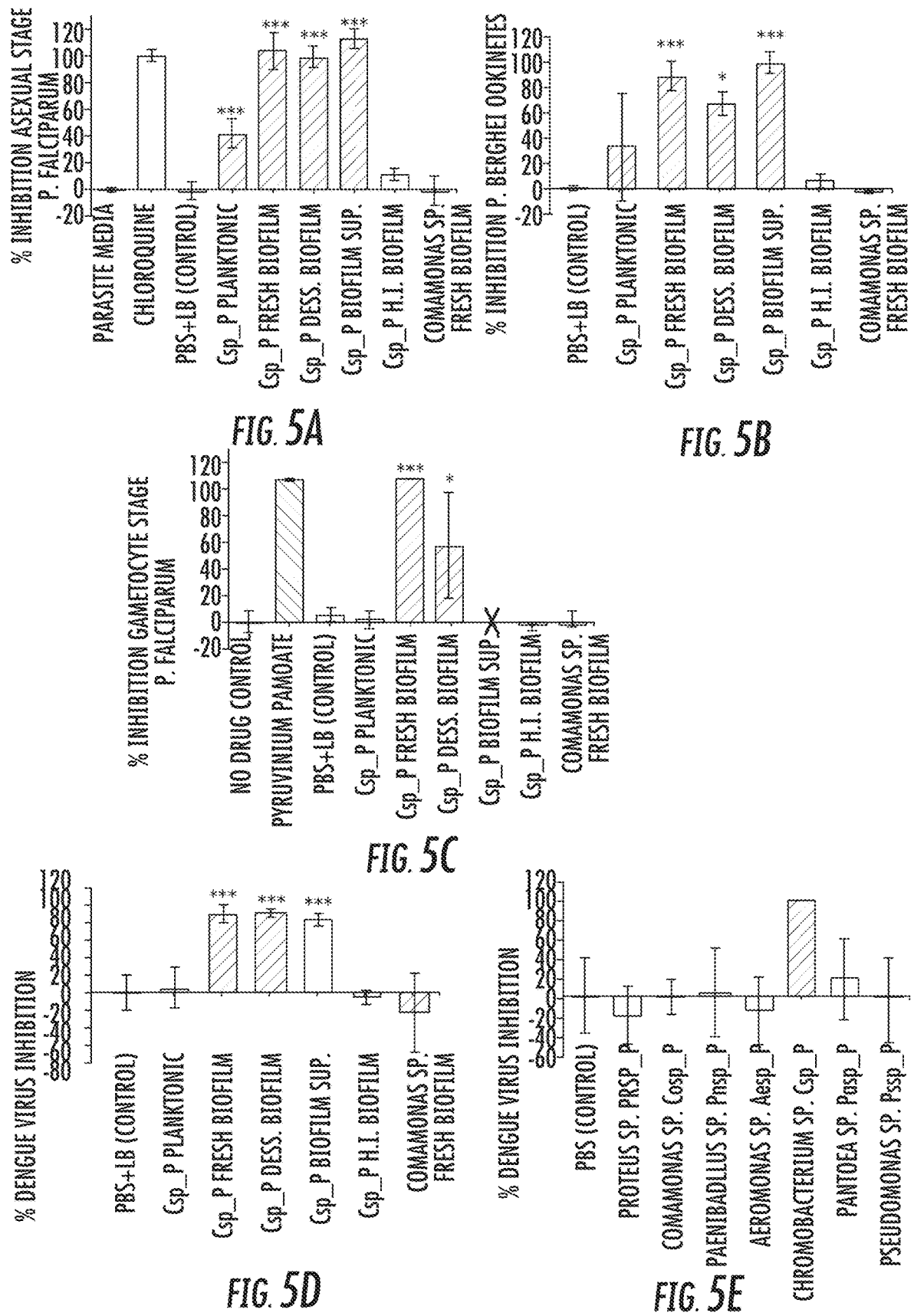
FIG. 5A-5E. Csp_P has anti-*Plasmodium* and anti-dengue activity in vitro. Csp_P was grown under planktonic and/or biofilm conditions and tested for anti-pathogen activity independent of the mosquito. Five different preparations of Csp_P were tested.
Figure 8:
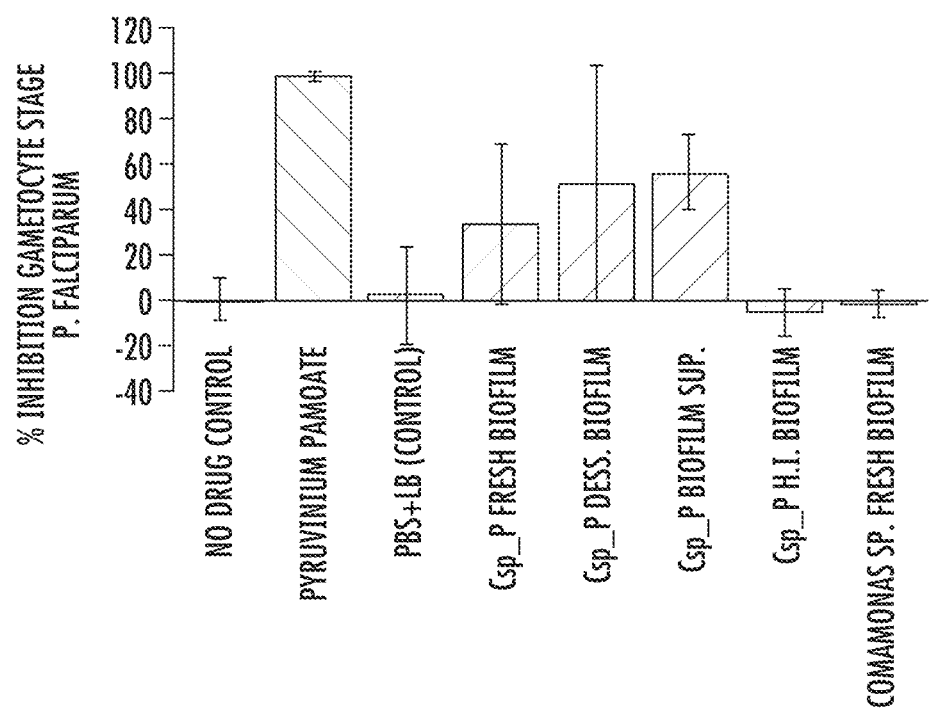
FIG. 8. Effect of 36-h biofilm on gametocyte-stage *P. falciparum*. Csp_P cultures were filtered using a 0.2-μm filter and mixed with gametocyte-stage *P. falciparum* cultures. Erythrocytes were examined for gametocytes using Giemsa-stained blood films collected 3 days after Csp_P exposure. We determined gametocyte density per 1000 RBCs for each sample and performed a Tukey's test to determine whether each bacterial treatment significantly differed from the PBS+LB control. No treatments were significant, but biofilm 36-h supernatant trended toward significance (p=0.06).

Our in vitro assays showed that Csp_P exerts potent anti-*Plasmodium* activity against both asexual and sexual parasite stages. We exposed *P. falciparum* 3D7 asexual stage parasites to all five bacterial preparations in vitro. Because bacterial growth can interfere with determining parasite number, we removed bacterial cells by filtering all preparations though a 0.2-μm filter. We found that all filtrates from 36-h biofilm preparations (fresh, supernatant, and desiccated) possessed strong anti-*Plasmodium* activity, resulting in inhibition of asexual stage parasites at a level comparable to the chloroquine-treated positive control (p<0.001, FIG. 5A). We also detected moderate anti-asexual stage activity in planktonic Csp_P preparations (p<0.001), while heat-inactivated Csp_P biofilm and biofilm from another bacterial species, *Comamonas* sp., had no inhibitory effect. We exposed an in vitro *Plasmodium* ookinete culture to all five filtered bacterial preparations to assess sexual-stage inhibition and found that the Csp_P 48-h biofilm (fresh, p<0.001; and desiccated, p<0.05) and biofilm supernatant (p<0.001) strongly blocked ookinete development (FIG. 5B). Exposure of the ookinete culture to the filtered planktonic Csp_P liquid culture resulted in a moderate but non-significant inhibition of ookinete development, and exposure to heat-inactivated Csp_P biofilm or *Comomonas* sp. biofilm filtrate had no effect on ookinete development (FIG. 5B). We also tested the effect of Csp_P bacterial preparations on *P. falciparum* gametocyte viability. Exposure to 42-h fresh biofilm filtrate resulted in 100% inhibition (p<0.001, FIG. 5C) and exposure to 42-h desiccated biofilm resulted in approximately 60% inhibition (p<0.05, FIG. 5C) of *P. falciparum* gametocyte development. Gametocytemia could not be estimated for 42-h biofilm supernatant because this preparation caused hemolysis of RBCs (FIG. 5C). However, 36-h biofilm supernatant (which is not hemolytic) caused approximately 60% gametocyte inhibition when compared to the LB+PBS control (p=0.06, FIG. 8).

Figure 9A:
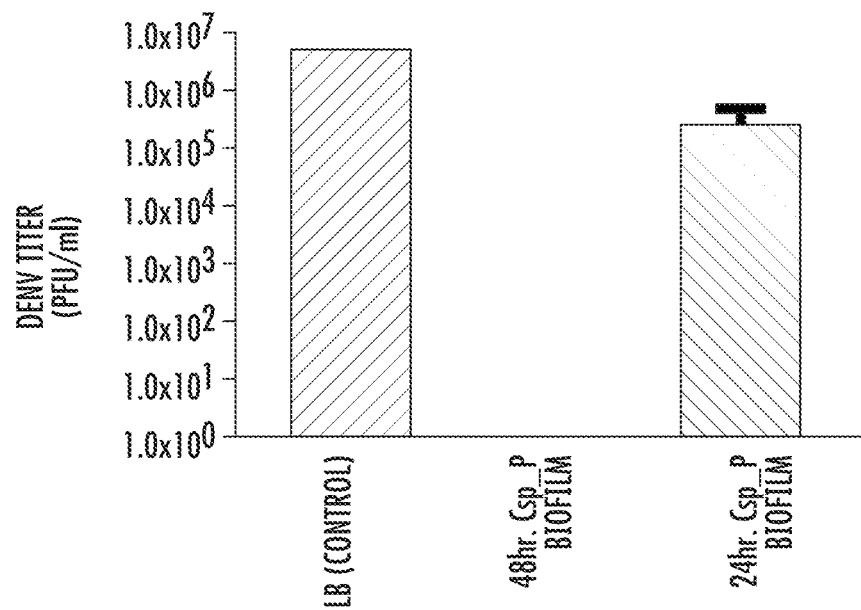
FIG. 9A-9B.

To test the inhibitory effect of Csp_P preparations on dengue virus infectivity in vitro, we mixed dengue virus ($10^6$ PFU/ml) in MEM 1:1 with each of the five bacterial preparations of Csp_P for 45 min. Samples remained unfiltered during initial exposure to dengue and were filtered through a 0.2-μm filter before proceeding with standard plaque assays to avoid contamination of host cells. We found that exposure of dengue virus to a planktonic Csp_P culture did not affect its infectivity in BHK21-15 cells, whereas exposure to Csp_P biofilm, desiccated biofilm, or biofilm supernatant did abolish dengue virus infectivity (p<0.001, FIG. 5D). To better replicate the effect that Csp_P biofilm might have on dengue virus in human blood, we exposed dengue virus in human blood to Csp_P fresh biofilm for 45 min. We then filtered the blood+virus/biofilm mixture and assessed dengue virus infectivity by standard plaque assay. We found that fresh Csp_P biofilm displayed strong anti-dengue activity when the virus was suspended in human blood (FIG. 5E). Csp_P fresh biofilm was unique in its anti-dengue activity, since the biofilms of several other bacterial isolates from the guts of field-caught mosquitoes did not exert any antiviral activity against dengue virus in human blood (FIG. 5E). The anti-dengue activity of Csp_P was apparently dependent on biofilm maturation, since biofilm grown for 24 h showed only weak inhibition when compared to 48-h biofilm (FIG. 9A). The Csp_P biofilm-associated anti-*Plasmodium* and antiviral activity was also heat-sensitive, since it could be inactivated through a 24-h incubation at 90° C. (FIG. 5A-D).

Figure 9B:
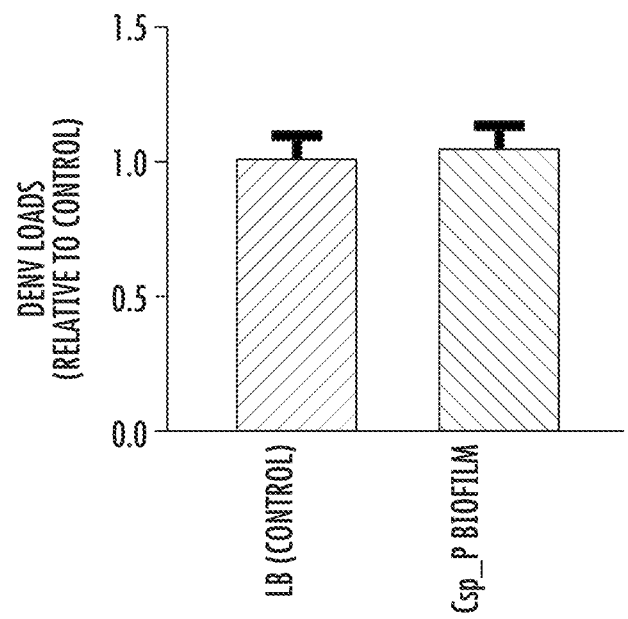
Figure 10A:
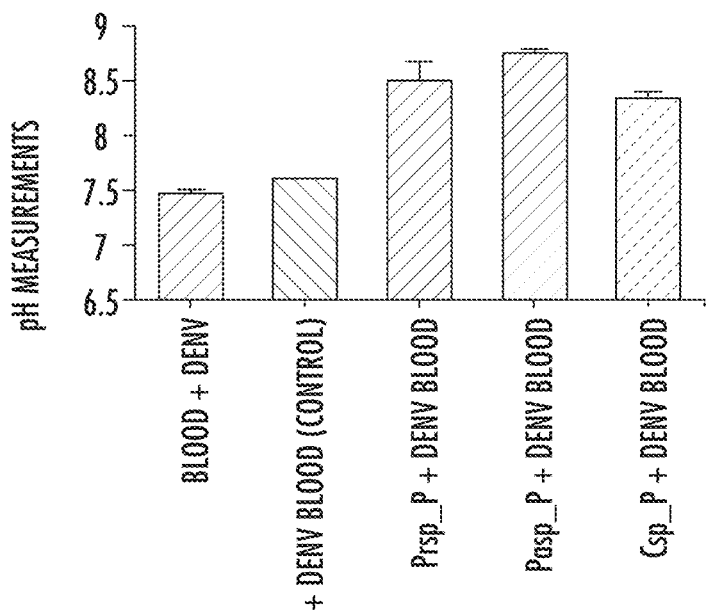
FIG. 10A-10B.
Figure 10B:
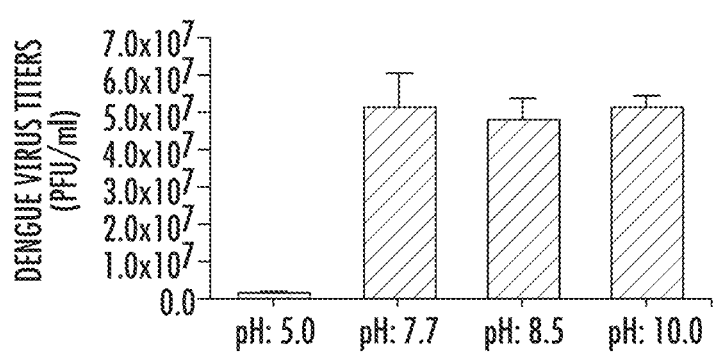
Figure 11A:
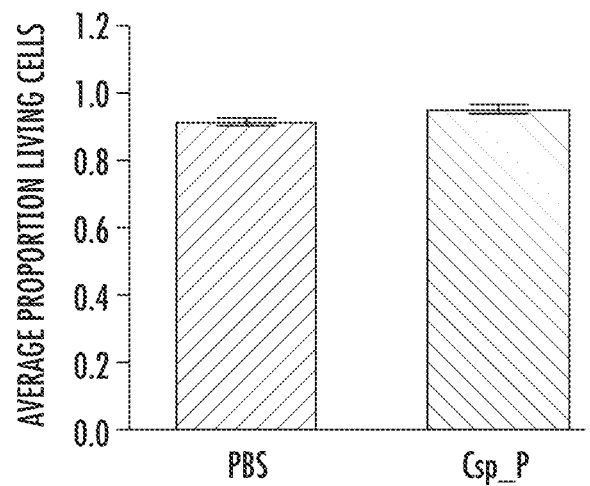
FIG. 11A-11B. Crude biofilm extract does not have cytotoxic effects on insect or mammalian cells. We used trypan blue staining (0.4%, Invitrogen) to assay cell viability of BHK21-15 cells (FIG. 11A) and C6/36 cells (FIG. 11B) after a 45 min exposure to filtered Csp_P fresh biofilm. Difference in cell viability due to Csp_P exposure were non-significant for both cell lines (Mann Whitney Test).
Figure 11B:
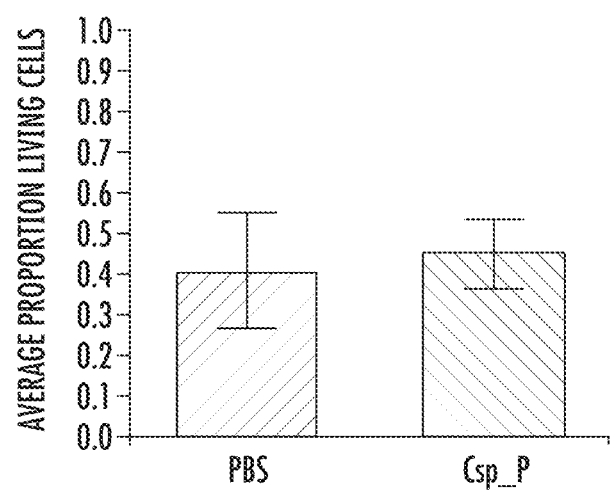
Figure 12:
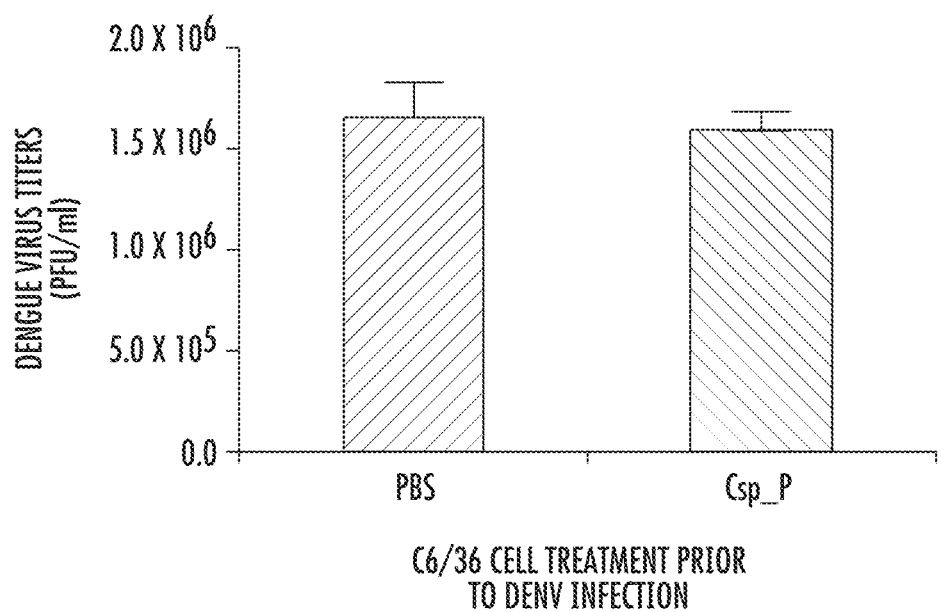
FIG. 12. Exposure to Csp_P biofilm does not alter the insect cells' susceptibility to dengue virus. We filtered Csp_P biofilm using a 0.2-μm filter and exposed C6/36 cells (grown to 80% confluency) to the bacterial filtrate for 45 min. Csp_P biofilm filtrate was then washed from the cells using 1×PBS, and cells were infected with dengue virus. Cells were assessed for plaque formation at 6 days post-infection.

Bacterial biofilms are composed of a matrix of extracellular polymeric substances containing polysaccharides, proteins, DNA, and secondary metabolites. To investigate whether the anti-viral activity could simply be a result of virus particle sequestration by the biofilm, we mixed a dengue virus suspension with biofilm and incubated the mixture for a period of 45 min. Samples were then centrifuged, and viral RNA in the supernatants was quantified by RT-qPCR and compared between experimental (biofilm+ DENV) and control (LB+DENV) treatments. Our results indicated that the dengue virus was not sequestered by Csp_P biofilm, since similar viral RNA copies were detected in the biofilm-exposed sample and the LB control sample (FIG. 9B). To investigate whether the loss of dengue virus infectivity was due to a biofilm-mediated change in the pH of the medium, we measured the pH of a dengue virus-Csp_P biofilm mixture at the end of a 45-min incubation period. The pH measurements showed an increase in the pH of the medium from 7.6 to 8.3 (FIG. 10A). A similar change in the pH was observed when we used the biofilms of other bacteria (*Pantoea* sp. Pasp_P and *Proteus* sp. Prsp_P) that do not affect dengue virus infectivity (FIG. 10A). To further investigate the effect of pH on dengue virus infectivity, we adjusted the pH of the MEM medium with NaOH and HCl to pH values of 5.0, 7.7, 8.5, and 10.0 prior to a 45-min incubation with the dengue virus. A decrease in virus infectivity was only observed after exposure to a pH of 5.0, suggesting that the moderate increase in pH did not mediate the Csp_P biofilm's inhibition of virus infectivity (FIG. 10B). We also showed that Csp_P biofilm does not exert a cytotoxic effect on insect or mammalian cells, as assessed by standard trypan blue cell staining (Invitrogen) (FIG. 11). We finally tested whether the Csp_P biofilm could influence the host cells' susceptibility to dengue virus infection by exposing C6/36 cells to Csp_P biofilm, then removing the biofilm through washes with PBS prior to dengue virus infection assays. This treatment did not influence the virus's ability to infect the host cells (FIG. 12), suggesting that the anti-DENV activity of Csp_P biofilm is not due to a reduced host cell susceptibility to the virus but is likely a direct anti-viral effect.

Csp_P Produces Broad-Spectrum Antibacterial Activity(ies).

Figure 6:
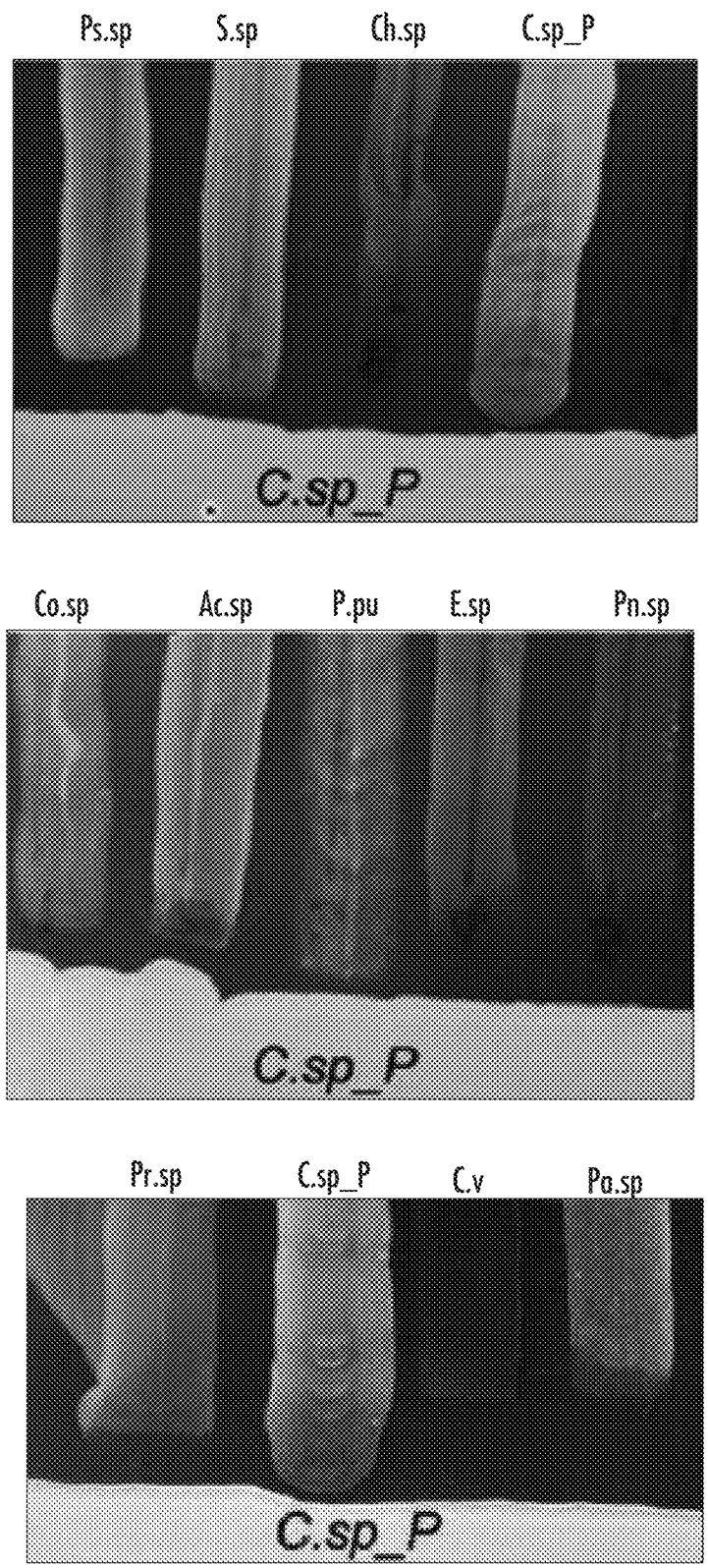
FIG. 6. Csp_P has anti-bacterial activity against many species commonly found in the midguts of *Aedes* and *Anopheles* mosquitoes. Csp_P was streaked on LB agar along with multiple bacterial species, and plates were observed for formation of zones of inhibition around Csp_P. Ps.sp=*Presudomonas* sp., Pr.sp=*Proteus* sp., Cs.p_P=*C.sp* P, C.viol=*C. violaceum*, Pa.sp=*Paenobacillus* sp., Co.sp=*Comamonas* sp., Ac.sp=*Acinetobacter* sp., Ps.pu *Pseudomonas putida*, En.sp *Enterobacter* sp., Pn.sp=*Pantoea* sp., Ps.sp=*Pseudomonas* sp., S.sp=*Serratia* sp., Ch.sp *Chryseobacterium* sp.

To provide baseline information on the potential production of antibacterial factors by Csp_P, we performed a basic growth inhibition assay by investigating the ability of a number of other mosquito midgut-derived bacterial isolates (*Ae. aegypti*-derived microbiota: Ps.sp=*Presudomonas* sp., Pr.sp=*Proteus* sp., Cs.p_P=*C.sp* P, C.viol=*C. violaceum*, Pa.sp=*Paenobacillus* sp.; *An. gambiae*-derived microbiota: Co.sp=*Comamonas* sp., Ac.sp=*Acinetobacter* sp., Ps.pu=*Pseudomonas putida*, En.sp *Enterobacter* sp., Pn.sp=*Pantoea* sp., Ps.sp=*Pseudomonas* sp., S.sp=*Serratia* sp., Ch.sp=*Chryseobacterium* sp.) to grow in proximity to Csp_P on LB agar plates (FIG. 6). Csp_P was streaked on LB agar and allowed to grow for 48 hours. Midgut-derived bacterial isolates were then vertically streaked up to the Csp_P streak, and allowed to grow in the presence of Csp_P. This assay showed a prominent growth inhibition zone around the Csp_P streak, with inhibition of the growth of all the bacterial isolates that were derived from field-collected *Ae. aegypti* and *An. gambiae*, including a close relative known for its production of a variety of bioactive factors, *C. violaceum* (FIG. 6A).

Conclusion

Insect-bacteria associations can influence vector competence in multiple ways; these include shortening the insect's life span, blocking infection with human pathogens by the production of bioactive anti-pathogen factors, and eliciting the insect immune system. We have identified a *Chromobacterium* sp_Panamam (Csp_P) bacterium from the midgut of field-derived *Aedes aegypti* that exerts broad-spectrum anti-pathogen activity against *Plasmodium* and dengue virus. Specifically, Csp_P renders *An. gambiae* and *Ae. aegypti* more resistant to infection by the human malaria parasite *Plasmodium falciparum*: and dengue virus, respectively. Csp_P inhibits the growth of a variety of other bacterial species found in the mosquito midgut and is capable of rapidly colonizing the mosquito midgut. Csp_P appears to exert entomopathogenic activity, since exposure of larvae to Csp_P in the breeding water and ingestion of Csp_P by adult mosquitoes result in high mosquito mortality. It is possible that Csp_P could be effectively used as a transmission blocking agent if it was delivered to mosquitoes through baited sugar traps. Csp_P's ability to colonize the mosquito gut could be further enhanced through established selection procedures based on consecutive passages of the bacterium through the mosquito intestine. Csp_P could be used alone in baited sugar traps or in combination with other microbes that have also been shown to either kill the mosquito or reduce pathogen infection, or both, when present in the mosquito gut. The larvicidal activity of Csp_P also renders it interesting for potential use in mosquito population suppression. The anti-pathogen activities of Csp_P appear to be mediated by bacteria-produced metabolites that also inhibit parasite and virus infection in vitro, making them interesting as possible lead compounds for transmission blocking and therapeutic drug development. The entomopathogenic, anti-bacterial, anti-viral, and anti-*Plasmodium* properties of Csp_P make this bacterium a particularly interesting candidate for the development of novel control strategies for the two most important vector-borne diseases, and they therefore warrant further in-depth study.

Figure 14:
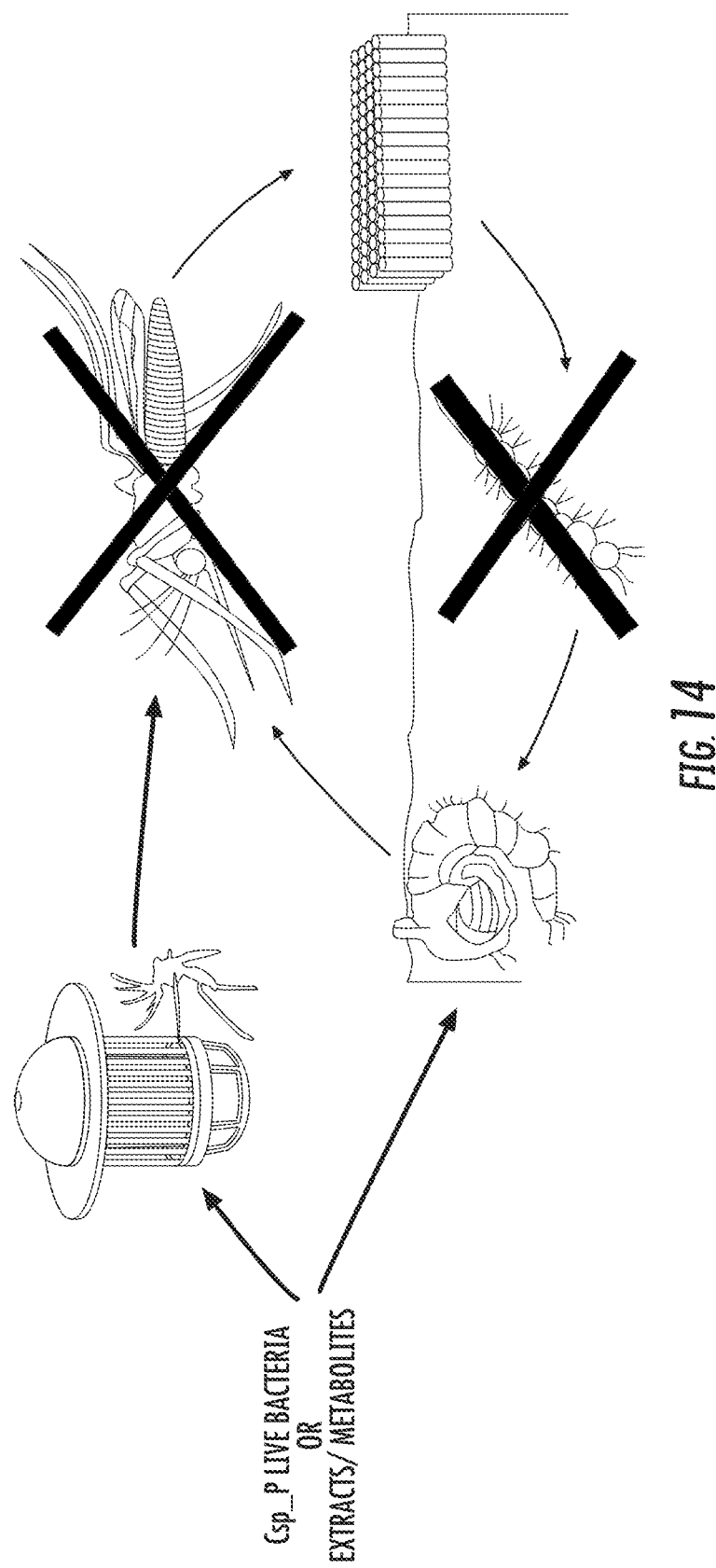
FIG. 14. Device for utilizing the versatility of Csp_P mosquitocidal activities that can target both larval and adult stages.
Figure 15D:
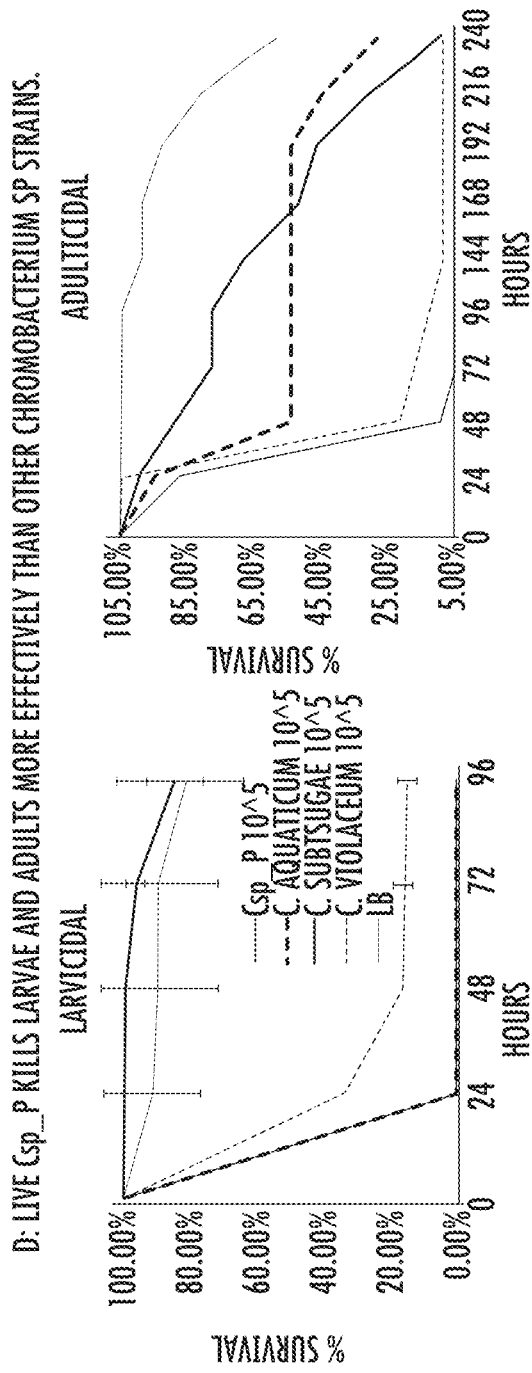

Example 2: Live *Chromobacterium* Csp_P is a General Mosquitocidal, and Malaria and Dengue Transmission-Blocking Agent Live *Chromobacterium* Csp_P can be easily exposed to adult mosquitoes through artificial sugar feeding and to larvae in the breeding water. Devices (sugar-bait stations) to expose mosquitoes to toxic agents have been developed and validated/used for mosquito control (FIG. 14). Exposure of adults to toxic agents through ingestion can also be achieved through direct spraying on the habitat, as in the case of Terminix's Attractive Targeted Sugar Bait which is widely used for mosquito control in the USA. Csp_P readily colonizes the gut or a large proportion of mosquitoes in a cage population when provided through artificial nectar feeding (FIG. 15A). Exposure of larvae or adult mosquitoes to Csp_P results in a significant killing (FIG. 15B). This killing activity has been validated for the malaria vectors *Anopheles gambiae* (African vector), *Anopheles stephensi* (Asian vector) and *Anopheles albimanus* (South American vector), the dengue vectors *Aedes aegypti* (worldwide vector) and *Aedes albopictus* (worldwide vector), and the West Nile Virus vector *Culex pipiens* (world-wide vector) (data not shown). Furthermore, the presence of Csp_P in adult *Anopheles* and *Aedes* gut tissue blocks *Plasmodium* and dengue virus infection, respectively (FIG. 15C). Hence, exposure of larvae and adult mosquitoes to Csp_P attenuates the transmission of disease by killing the vector and by blocking the pathogen in the vector (FIGS. 15B and 15C). The combined larvicidal and adulticidal activities of Csp_P is more potent than that of other studied *Chromobacterium* sp strains, including *Cromobacterium* subtsugae which is the active component of the agricultural biopesticide Grandevo which is marketed by Marrone Bio Innovations (FIG. 15D).

Figure 16A:
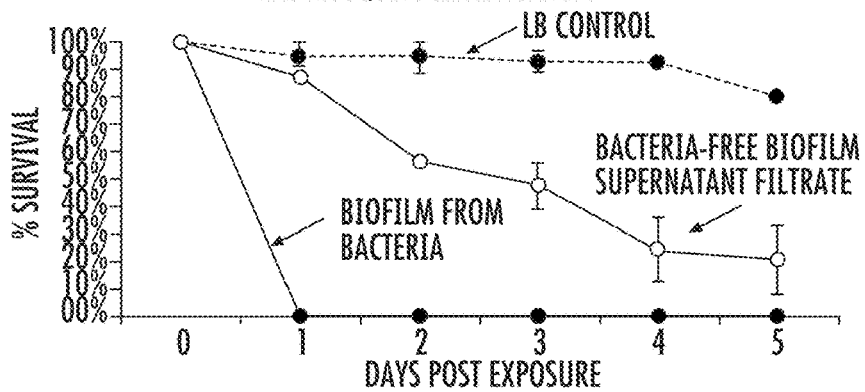
FIG. 16A-16C. Secreted *Chromobacterium* Csp_P metabolites have mosquitocidal activity. Exposure of adult mosquitoes to a Csp_P bacteria-free biofilm culture supernatant through artificial nectar feeding results in significant killing, indicating the presence of mosquitocidal agents in the filtrate preparation (FIG. 16A). Reverse Phase Liquid Chromatography (RPLC) of the Csp_P bacteria-free biofilm culture supernatant identifies several metabolite peaks that may contain one or more Csp_P biofilm culture secreted metabolites (FIG. 16B). Mosquitocidal assays with pools of RPLC fractions that contain metabolite peaks identified one fraction pool that kill adult mosquitoes upon ingestion through an artificial nectar (FIG. 16C).
Figure 16B:
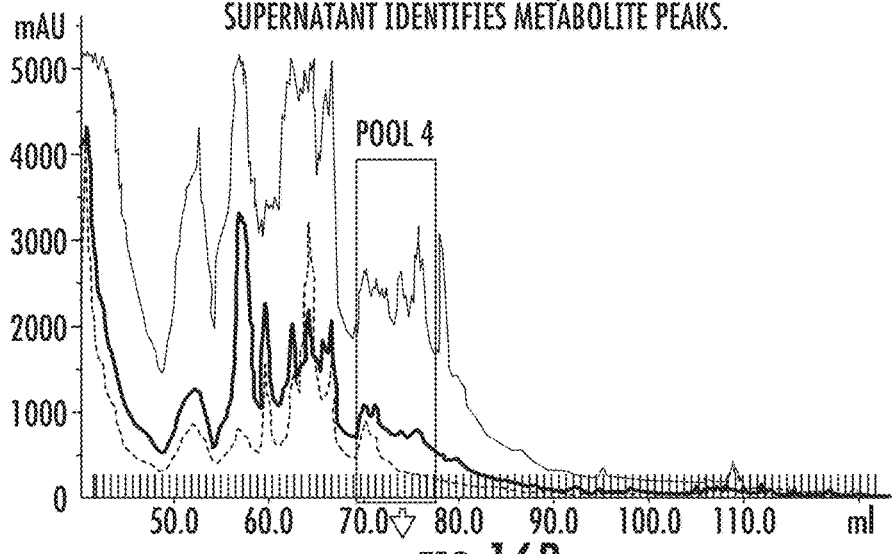
Figure 16C:
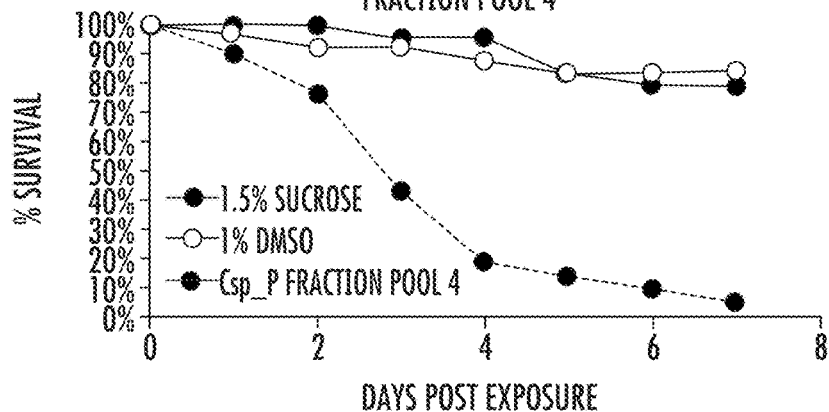

Secreted *Chromobacterium* Csp_P Metabolites have Mosquitocidal Activity. Exposure of adult mosquitoes to a Csp_P bacteria-free biofilm culture supernatant through artificial nectar feeding results in significant killing, indicating the presence of mosquitocidal agents in the filtrate preparation (FIG. 16A). Csp_P likely secrets stable metabolites with mosquitocidal activity. Reverse Phase Liquid Chromatography (RPLC) of the Csp_P bacteria-free biofilm culture supernatant identifies several metabolite peaks that may contain one or more Csp_P biofilm culture secreted metabolites (FIG. 16B). Mosquitocidal assays with pools of RPLC fractions that contain metabolite peaks identified one fraction pool that kill adult mosquitoes upon ingestion through an artificial nectar (FIG. 16C). This fraction pool likely contains the mosquitocidal metabolite and is subjected to further fractionation and bioassays to define the active component(s).

The versatility of Csp_P mosquitocidal activities that can target both larval and adult stages is unique, in contrast to the widely used mosquitocidal biopesticides which are based on live *Bacillus thuringiensis* and *Bacillus sphaericus* bacteria that only act against the larval stages. Mosquito resistance has been observed for both *Bacillus thuringiensis* and *Bacillus sphaericus*. The pathogen-blocking activity of Csp_P in the mosquito gut further potentiates its utility for mosquito-based malaria and dengue transmission blocking (FIG. 14).

We claim:

1. A method for controlling mosquitoes comprising applying in an area where the mosquitoes are to be controlled a composition comprising an effective insect control amount of a supernatant, filtrate or extract of a biologically pure culture of Chromobacterium sp_Panamam (Csp_P).

2. The method of claim 1, wherein the composition further comprise a mosquito nectar feed.

3. The method of claim 2, wherein the mosquito nectar feed comprises sucrose, dextrose and/or fructose.

4. The method of claim 1, wherein the Csp_P is the bacteria having the characteristics of ATCC Designation No. PTA-121570.

5. The method of claim 1, wherein the Csp_P has the 16s rDNA gene sequence of SEQ ID NO:1.

* * * * *